US008812124B2

(12) United States Patent
Lee

(10) Patent No.: US 8,812,124 B2
(45) Date of Patent: *Aug. 19, 2014

(54) NEUROSTIMULATION SYSTEM AND METHOD FOR MEDIO-LATERALLY STEERING CURRENT USING IDEAL MULTIPOLE CONFIGURATIONS

(75) Inventor: Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/420,209

(22) Filed: Mar. 14, 2012

(65) Prior Publication Data
US 2012/0239114 A1    Sep. 20, 2012

Related U.S. Application Data

(60) Provisional application No. 61/453,004, filed on Mar. 15, 2011.

(51) Int. Cl.
*A61N 1/372*    (2006.01)
*A61N 1/36*    (2006.01)
*G06F 19/00*    (2011.01)

(52) U.S. Cl.
CPC ........ *A61N 1/36185* (2013.01); *G06F 19/3406* (2013.01); *A61N 1/37247* (2013.01)
USPC .............................................. 607/59; 607/45

(58) Field of Classification Search
USPC ...................................................... 607/45, 59
See application file for complete search history.

(56) References Cited

U.S. PATENT DOCUMENTS

| 5,895,416 | A | 4/1999 | Barrers, Sr. et al. |
| 6,516,227 | B1 | 2/2003 | Meadows et al. |
| 6,895,280 | B2 | 5/2005 | Meadows et al. |
| 6,993,384 | B2 | 1/2006 | Bradley et al. |

(Continued)

FOREIGN PATENT DOCUMENTS

| WO | WO 2008/070140 A2 | 6/2008 |
| WO | WO 2008070140 | 6/2008 |
| WO | WO 2008/091268 A1 | 7/2008 |
| WO | WO 2008091268 | 7/2008 |

OTHER PUBLICATIONS

U.S. Appl. No. 61/374,879, Title: User Interface for Segmented Neurostimulation Leads, Inventor: Michael A. Moffitt et al., filed Aug. 18, 2010.

(Continued)

*Primary Examiner* — Joseph Dietrich
(74) *Attorney, Agent, or Firm* — Vista IP Law Group LLP

(57) ABSTRACT

A system for an electrical neurostimulator coupled to a plurality of electrodes. The system comprises a user-controlled input device configured for generating directional control signals. The system further comprises control circuitry configured for sequentially defining a plurality of different ideal multipole configurations that includes two orthogonal ideal tripole configurations relative to the plurality of electrodes in response to the directional control signals, generating a plurality of stimulation parameter sets respectively corresponding to the plurality of different ideal multipole configuration, each stimulation parameter set defining relative amplitude values for the plurality of electrodes that emulate the respective multipole configuration, and instructing the electrical neurostimulator to convey electrical energy to the plurality of electrodes in accordance with the plurality of stimulation parameter sets.

28 Claims, 23 Drawing Sheets

(56) References Cited

U.S. PATENT DOCUMENTS

| | | |
|---|---|---|
| 7,650,184 B2 | 1/2010 | Walter |
| 7,987,000 B2 | 7/2011 | Moffitt et al. |
| 2007/0150036 A1 | 6/2007 | Anderson |
| 2007/0168004 A1 | 7/2007 | Walter |
| 2008/0163097 A1* | 7/2008 | Goetz et al. ............ 715/772 |
| 2008/0183256 A1* | 7/2008 | Keacher ............ 607/116 |
| 2010/0010566 A1 | 1/2010 | Thacker et al. |
| 2010/0023097 A1 | 1/2010 | Peterson et al. |
| 2010/0057162 A1 | 3/2010 | Moffitt et al. |
| 2010/0121409 A1 | 5/2010 | Kothandaraman et al. |
| 2011/0106215 A1 | 5/2011 | Moffitt |
| 2012/0239109 A1 | 9/2012 | Lee |
| 2012/0239110 A1 | 9/2012 | Lee |
| 2012/0239115 A1 | 9/2012 | Lee |
| 2012/0239116 A1 | 9/2012 | Lee et al. |

OTHER PUBLICATIONS

U.S. Appl. No. 61/452,965, Title: Neurostimulation System for Defining Generalized Ideal Multipole Configurations, Inventor: Dongchul Lee, filed Mar. 15, 2011.

U.S. Appl. No. 61/453,015, Title: Neurostimulation System for Defining Ideal Multipole Configurations at Lead Boundary, Inventor: Dongchul Lee, filed Mar. 15, 2011.

U.S. Appl. No. 61/453,025, Title: Neurostimulation System for Matching Ideal Pole Spacing with Effective Electrode Separation, Inventor: Dongchul Lee et al., filed Mar. 15, 2011.

U.S. Appl. No. 61/452,989, Title: Neurostimulation System and Method for Rostro-Caudally Steering Current Using Longitudinal Ideal Multipole Configurations, Inventor: Dongchul Lee, filed Mar. 15, 2011.

Annex to Form PCT/ISA/206 issued in PCT/US2012/029290, Applicant: Boston Scientific Neuromodulation Corporation, Form PCT/ISA/2206 (Annex), Jun. 27, 2013 (5pages).

File History for U.S. Appl. No. 13/420,312, filed Mar. 14, 2012, Inventor: Dongchul Lee.

File History for U.S. Appl. No. 13/420,060, filed Mar. 14, 2012, Inventor: Dongchul Lee.

Office Action dated Mar. 28, 2013 in U.S. Appl. No. 13/420,060, filed Mar. 14, 2012, Inventor: Dongchul Lee, (10pages).

File History for U.S. Appl. No. 13/420,258, filed Mar. 14, 2012, Inventor: Dongchul Lee.

Office Action dated Mar. 29, 2013 in U.S. Appl. No. 13/420,258, filed Mar. 14, 2012, Inventor: Dongchul Lee, (10pages).

File History for U.S. Appl. No. 13/420,140, filed Mar. 14, 2012, Inventor: Dongchul Lee.

Office Action dated Mar. 28, 2013 in U.S. Appl. No. 13/420,140, filed Mar. 14, 2012, Inventor: Dongchul Lee, (10pages).

PCT International Search Report for PCT/US2012/029290, Applicant: Boston Scientific Neuromodulation Corporation, Form PCT/ISA/210 and 220, dated Sep. 18, 2013 (6pages).

PCT Written Opinion of the International Search Authority for PCT/US2012/029290, Applicant: Boston Scientific Neuromodulation Corporation, Form PCT/ISA/237, dated Sep. 18, 2013 (11pages).

PCT International Preliminary Report on Patentability (Chapter I of the Patent Cooperation Treaty) for PCT/US2012/029290, Applicant: Boston Scientific Neuromodulation Corporation, Form PCT/IB/326 and 373, dated Oct. 3, 2013 (13pages).

Office Action dated Oct. 1, 2013 in U.S. Appl. No. 13/420,060, filed Mar. 14, 2012, inventor: Dongchul Lee, (11pages).

Office Action dated Oct. 1, 2013 in U.S. Appl. No. 13/420,140, filed Mar. 14, 2012, inventor: Dongchul Lee, (11pages).

Office Action dated Oct. 2, 2013 in U.S. Appl. No. 13/420,258, filed Mar. 14, 2012, inventor: Dongchul Lee, (11pages).

Office Action dated Oct. 4, 2013 in U.S. Appl. No. 13/420,312, filed Mar. 14, 2012, inventor: Dongchul Lee, (14pages).

* cited by examiner

A2 = 100 − A1
LGF: Longitudinal focus

- Transition point between critical points
- ○ Critical points
- Cathode shifting points

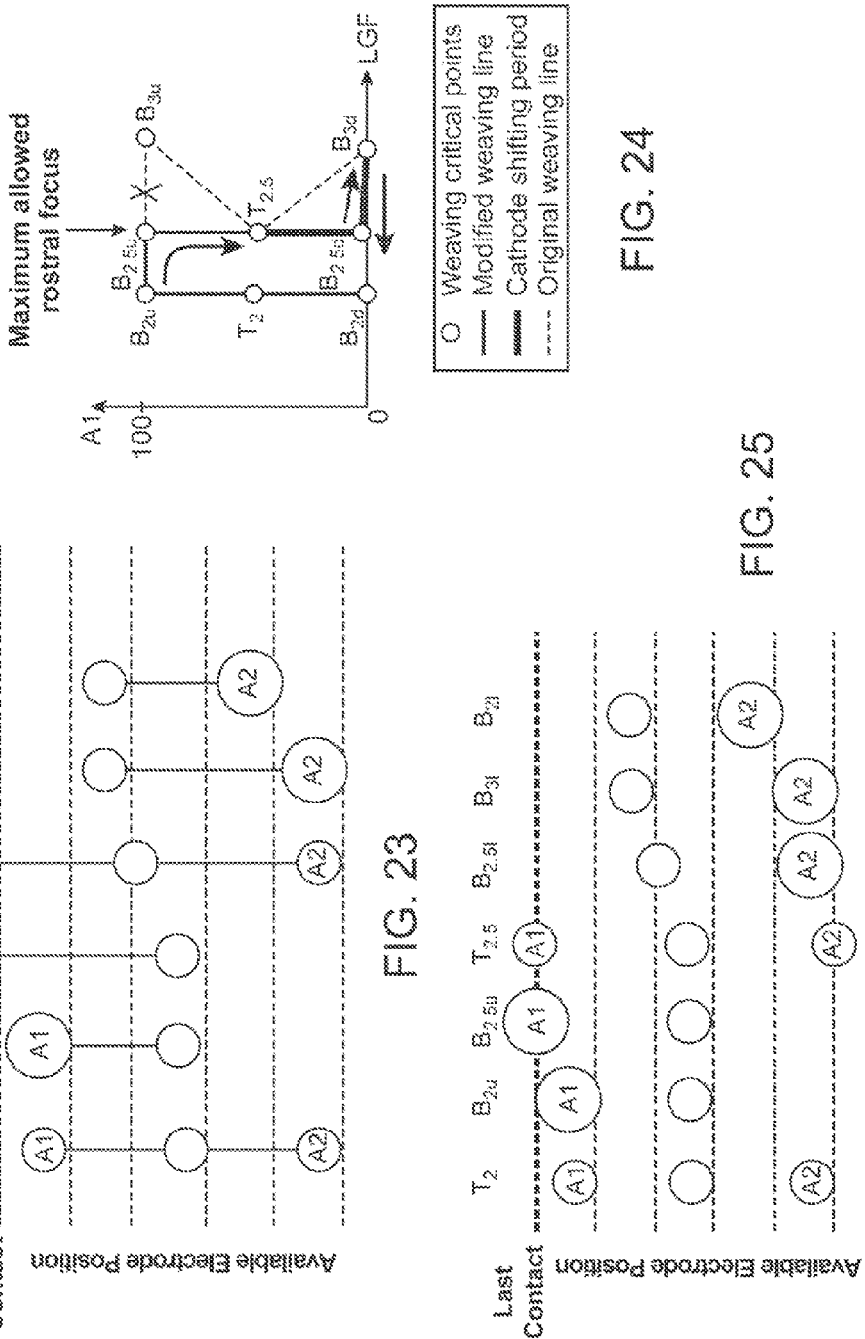
FIG. 24
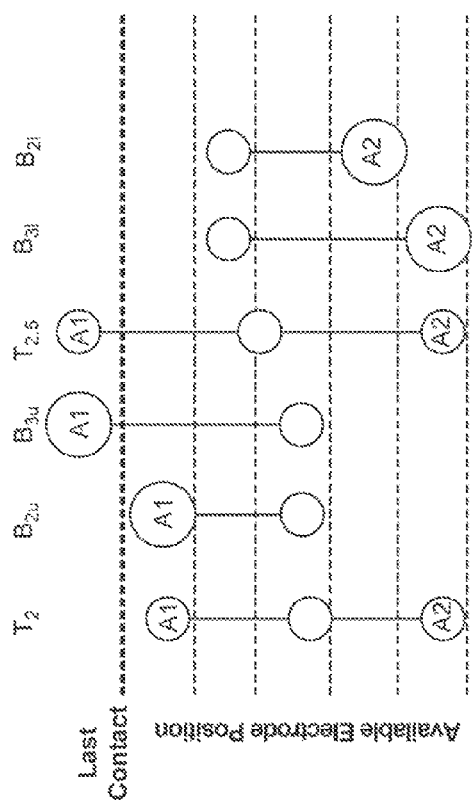
FIG. 23
FIG. 25

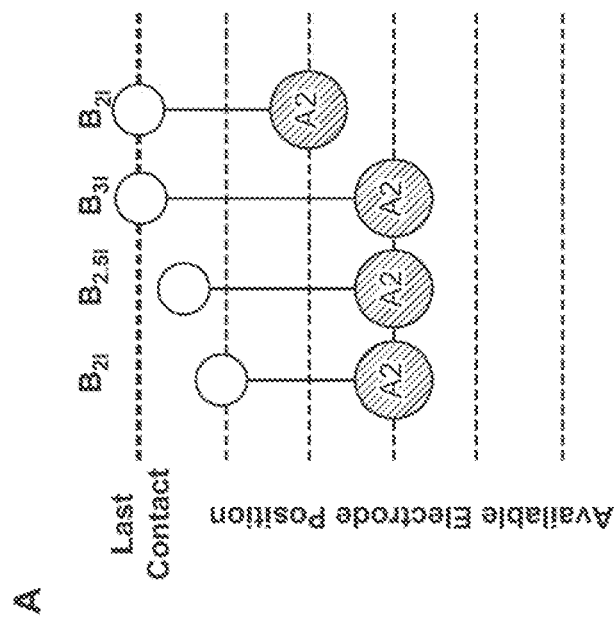
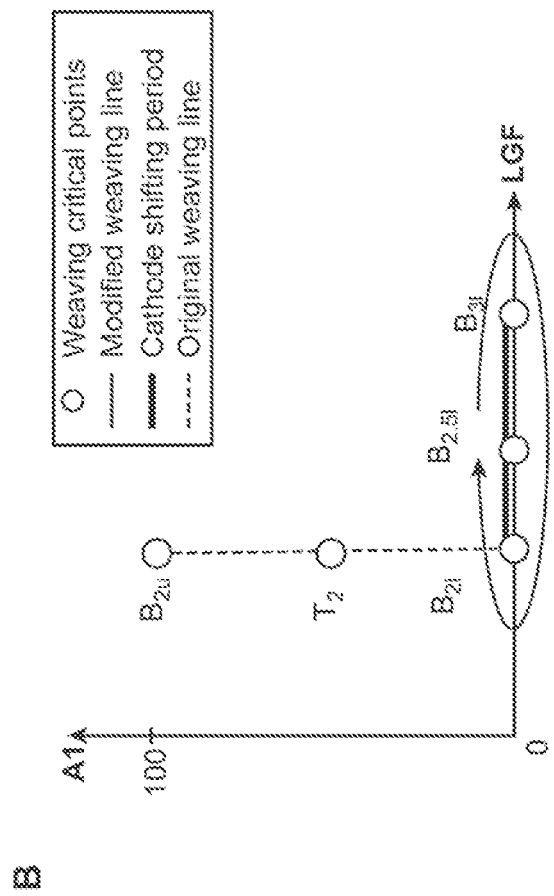
FIG. 29
FIG. 30

NEUROSTIMULATION SYSTEM AND METHOD FOR MEDIO-LATERALLY STEERING CURRENT USING IDEAL MULTIPOLE CONFIGURATIONS

RELATED APPLICATIONS

The present application claims the benefit under 35 U.S.C. §119 to U.S. Provisional Patent Application Ser. No. 61/453,004, filed Mar. 15, 2011. The foregoing application is hereby incorporated by reference into the present application in its entirety. The present utility application is filed concurrently with U.S. patent application Ser. No. 13/420,060, entitled "NEUROSTIMULATION SYSTEM FOR DEFINING A GENERALIZED IDEAL MULTIPOLE CONFIGURATION", U.S. patent application Ser. No. 13/420,040, entitled "NEUROSTIMULATION SYSTEM AND METHOD FOR ROSTRO-CAUDALLY STEERING CURRENT", U.S. patent application Ser. No. 13/420,258, entitled "NEUROSTIMULATION SYSTEM FOR DEFINING IDEAL MULTIPOLE CONFIGURATIONS AT LEAD BOUNDARY", and U.S. patent application Ser. No. 13/420,312, entitled "NEUROSTIMULATION SYSTEM FOR MATCHING IDEAL POLE SPACING WITH EFFECTIVE ELECTRODE SEPARATION", the disclosures of which are expressly incorporated herein by reference.

FIELD OF THE INVENTION

The present inventions relate to tissue stimulation systems, and more particularly, to neurostimulation systems for programming neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. In the context of SCS, current steering is typically either performed in a rostro-caudal direction (i.e., along the axis of the spinal cord) or a medial-lateral direction (i.e., perpendicular to the axis of the spinal cord). The Bionic Navigator® may use one of two ways to electrically steer the current along the implanted leads.

In one current steering method, known as "weaving," the anode or anodes are moved around the cathode, while the cathode slowly progresses down the sequence of electrodes. In the context of SCS, the active electrode combinations typically used to implement the weaving sequence includes a narrow tripole (tightly spaced center cathode and two flanking anodes), narrow upper bipole (tightly spaced anode above cathode), wide upper bipole (widely spaced anode above cathode), wide tripole (widely spaced center cathode and two flanking anodes), wide lower bipole (widely spaced anode below cathode), narrow lower bipole (narrowly spaced anode below cathode). In another current steering method, known as "panning," a pre-defined electrode combination is shifted down the sequence of electrodes without changing the basic form of the electrode combination. These current steering methods may have different clinical uses (e.g., finding the "sweet spot" in the case of panning, or shaping the electrical field around the cathode in the case of weaving).

In the context of SCS, a volume of activation (VOA) will typically be displaced in concordance with the displacement of the cathode or group of cathodes as electrical current is steering in a particular direction. In one method, the VOA may be rostro-caudally displaced along the spinal cord of the patient using, e.g., the weaving or panning steering current steering methods, in order to stimulate the rostro-caudal dermatome associated with the ailment to be treated. In another method known as Transverse Tripole Stimulation (TTS), wherein a tripole electrode configuration consisting of a central cathode and two flanking anodes is used, to selectively stimulate dorsal column (DC) nerve fibers without stimulating the dorsal root (DR) nerve fibers typically associated with painful or otherwise uncomfortable side-effects. To target a population of DC nerve fibers where medio-lateral fiber distribution is mapped into rostro-caudal dermatomes, steering of current onto the DC nerve fibers is a critical component of TTS. Typically, in the three-column electrode arrangement, steering of current in TTS can be achieved by adjusting the intensity of the flanking anodes, as described in U.S. patent application Ser. No. 12/508,407, entitled "System and Method for Increasing Relative Intensity Between Cathodes and Anodes of Neurostimulation System," which is expressly incorporated herein by reference.

The Bionic Navigator® presently performs current steering in accordance with a steering or navigation table. For example, an exemplary navigation table, which includes a series of reference electrode combinations (e.g., for a lead of 8 electrodes) with associated fractionalized current values (i.e., fractionalized electrode configurations), can be used to gradually steer electrical current from one basic electrode combination to the next, thereby electronically steering the volume of activation (VOA) along the leads.

While the use of navigation tables have proven to be useful in steering electrical current between electrodes in an efficient manner, that are certain inherent disadvantages associated with navigation tables. For example, assuming a current step size of 5% in the navigation table, there are literally billions of fractionalized electrode configurations that can be selected. However, due to memory and time constraints, only a limited number of fractionalized electrode configurations are stored within the navigation table. Therefore, not every desired electrode combination and associated fractionalized current values can be represented within a steering table.

Furthermore, a substantial amount of time and effort must be spent in developing navigation tables for each new lead design, thereby presenting a bottleneck for lead development. For example, each steering table must take into account the variability in electrode position or stimulation input. The variability in electrode position may be due to, e.g., a different lead model, different lead configurations (e.g., a closely spaced side-by-side configuration, a closely spaced top-bottom configuration, a widely spaced top-bottom configuration, or a widely spaced side-by-side configuration), stagger of the leads, etc. The variability in stimulation input may be due to, e.g., the development or inclusion of additional steerable fields (e.g., medio-lateral tripole steering), upgrades in steering controls (e.g., focusing/blurring of fields, anode intensification or de-intensification (i.e., increasing or decreasing local anodic current relative to cathodic current), current steering from different screens, etc. Because the implementation of new navigation tables must take into account all leads that are to be used with the IPG, as well as the different lead positions, this challenge slows the ability to include new navigation features in the system.

Furthermore, if the remote control needs to be reprogrammed; for example, if the patient returns to a physician's office to be refitted to improve the stimulation therapy provided by the neurostimulator, the clinician may have to start the fitting from scratch. In particular, while the remote control is capable of uploading the stimulation parameter sets to the Bionic Navigator® to aid in reprogramming the remote control, they may be different from any stimulation parameter sets that are capable of being generated using the navigation table due to the limited number of fractionalized electrode configurations within the navigation table; that is, the fractionalized electrode configurations currently stored in the remote control may not match any fractionalized electrode configurations stored in the navigation table because they were originally generated when the Bionic Navigator® was operated in the manual mode.

In any event, if the stimulation parameter sets uploaded from the remote control to the Bionic Navigator® do not identically match any stimulation parameter set corresponding to a fractionalized electrode configuration stored in the navigation table, it cannot be used as a starting point in reprogramming the remote control/IPG. As a result, the amount of time required to reprogram the remote control/IPG may be as long as the amount of time required to originally program the remote control/IPG with the Bionic Navigator®. Because programming the remote control can be quite complex, even when the Bionic Navigator® is operated in the navigation mode, the time lost as a result of having to reprogram the remote control/IPG from scratch, can be quite significant.

In one novel method, described in U.S. Pat. No. 8,412,345, which is incorporated herein by reference, a stimulation target in the form of an ideal target pole (e.g., an ideal bipole or tripole) is defined and the stimulation parameters, including the fractionalized current values on each of the electrodes, are computationally determined in a manner that emulates these ideal target poles. It can be appreciated that current steering can be implemented by moving the ideal target poles about the leads, such that the appropriate fractionalized current values for the electrodes are computed for each of the various positions of the ideal target pole. As a result, the current steering can be implemented using an arbitrary number and arrangement of electrodes, thereby solving the afore-described problems.

While the computation of stimulation parameters to emulate ideal target poles is quite useful, there remains a need to provide a more generalized format for ideal target poles to provide more flexibility to steering current in an arbitrary direction. For example, ideal target poles aligned along the longitudinal axis of the spinal cord of a patient may be optimum when steering current in a rostro-caudal (longitudinal) direction, but may not be optimum when steering current in a medial-lateral (transverse) direction. Likewise, ideal target poles aligned perpendicular to the longitudinal axis of the spinal cord of a patient may be optimum when steering current in a medial-lateral (transverse) direction, but may not be optimum when steering current in a rostro-caudal direction (longitudinal). There also remains a need for improved techniques using ideal target poles to steer current in the rostro-caudal direction and the medial-lateral direction.

Furthermore, because there a limited number of electrodes when steering current in a particular direction using arbitrarily defined target poles, there remains a need to modify the current steering on-the-fly to prevent any target poles from being moved outside the maximum extent of the electrode array. Also, for ideal multipole configurations, which include at least one ideal cathode and at least one ideal anode, it is desirable to match the spacing between the ideal cathode(s) and ideal anode(s) with the spacing of the physical electrodes in order to minimize dilution of the electrical current on multiple electrodes, which may otherwise cause amplitude fluctuation or a non-focused stimulation region during current steering. However, because different types of neurostimulation leads have different electrode separations, a current steering algorithm that is designed for a particular electrode separation cannot be used for other electrode separations. Furthermore, when multiple neurostimulation leads are used, the spacings between the electrodes will typically not be uniform, thereby providing a challenge when attempting to match the ideal cathode/anode spacings with the spacings of the physical electrodes.

SUMMARY OF THE INVENTION

In accordance with one aspect of the present inventions, a system for an electrical neurostimulator coupled to a plurality of electrodes is provided.

The system comprises a user-controlled input device configured for generating directional control signals. In one embodiment, the user-control input device includes a control element, a continual actuation of which generates the control signals. The user-controlled input device may comprise, e.g., one or more of a graphical arrow, a joystick, a touchpad, a button pad, a group of keyboard arrow keys, a mouse, a roller ball tracking device, and horizontal and vertical rocker-type arm switches for generating the directional control signals. The system further comprises control circuitry configured for sequentially defining a plurality of different ideal multipole configurations that includes two orthogonal ideal tripole configurations relative to the plurality of electrodes in response to the directional control signals.

In one embodiment, the control circuitry may be configured for sequentially defining the different multipole configurations in the following order: a first ideal tripole configuration oriented in a first direction, a second ideal tripole configuration oriented in the first direction, a third ideal tripole configuration oriented in a second direction orthogonal to the first direction, and a fourth ideal tripole configuration oriented in the second direction. In this case, the first ideal tripole configuration may be a narrow symmetrical ideal tripole configuration, the second ideal tripole configuration may be a narrow asymmetrical ideal tripole configuration, the third ideal tripole configuration may be a narrow symmetrical ideal tripole configuration, and the fourth ideal tripole configuration may be a wide symmetrical ideal tripole configuration.

The control circuitry may be configured for incrementally changing a position of a central ideal cathode relative to the plurality of electrodes between the first ideal tripole configuration and the second ideal tripole configuration, maintaining the same position of a central ideal cathode relative to the plurality of electrodes between the second ideal tripole configuration and the third ideal tripole configuration, incrementally changing a position of a central ideal cathode relative to the plurality of electrodes between the third ideal tripole configuration and the fourth ideal tripole configuration.

In an optional embodiment, the control circuitry is configured for defining a quadpole configuration after the fourth ideal tripole configuration in response to the control signals. In this case, the control circuitry may be configured for maintaining the same positions of a central cathode and two anodes relative to the plurality of electrodes between the fourth ideal tripole configuration and the ideal quadpole configuration. The quadpole configuration may include an anode positioned equidistant between the two anodes.

The control circuitry is further configured generating a plurality of stimulation parameter sets respectively corresponding to the ideal multipole configurations, with each stimulation parameter set defining relative amplitude values for the plurality of electrodes that emulate the respective ideal multipole configuration, and instructing the electrical neurostimulator to convey electrical energy to the plurality of electrodes in accordance with the plurality of stimulation parameter sets. In an optional embodiment, the system further comprises telemetry circuitry, wherein the control circuitry is configured for transmitting the stimulation parameter sets to the neurostimulation device via the telemetry circuitry. In another optional embodiment, the system further comprises a housing containing the user input device, the memory, and the control circuitry.

In accordance another aspect of the present inventions, a method of providing therapy to a patient using a plurality of electrodes implanted adjacent a spinal cord of the patient is provided. The method comprises generating directional control signals, e.g., by continually actuating a control element to generate the directional control signals. The method comprises sequentially defining a plurality of different ideal multipole configurations relative to the plurality of electrodes in response to the directional control signals, wherein the plurality of different ideal multipole configurations includes a first ideal tripole configuration medio-laterally oriented relative to the spinal cord and a second ideal tripole configuration rostro-caudally oriented relative to the spinal cord. The details of the multipole configurations may be the same as those discussed above.

The method further comprises generating a plurality of stimulation parameter sets respectively corresponding to the ideal multipole configurations, and instructing the electrical neurostimulator to convey electrical energy to the plurality of electrodes in accordance with the plurality of stimulation parameter sets, thereby emulating the respective ideal multipole configurations. In the context of SCS, the conveyance of the electrical energy to the plurality of electrodes in accordance with the plurality of stimulation parameter sets may incrementally medio-laterally displace a volume of activation (VOA) across a spinal cord of the patient.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 23 is still another sequence of different ideal bipole/tripole configurations that can be derived from the ideal longitudinal tripole of FIG. 14 to rostro-caudally displace a volume of activation, wherein one of the ideal bipole/tripole configurations exceeds the maximum extent of the electrode array;

FIG. 24 is a corrected sequence of the ideal bipole/tripole configurations shown in FIG. 23, wherein none of the ideal bipole/tripole configurations exceeds the maximum extent of the electrode array;

FIG. 25 is a plot illustrating a weaving space for the sequence of ideal bipole/tripole configurations illustrated in FIG. 24;

FIG. 29 is a corrected sequence of the ideal bipole/tripole configurations shown in FIG. 23, wherein the ideal tripole configurations and the ideal upper ideal bipole configurations are eliminated to prevent the ideal bipole/tripole configurations from exceeding the maximum rostral extent of the electrode array;

FIG. 30 is a plot illustrating a weaving space for the sequence of lower ideal bipole configurations illustrated in FIG. 29;

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neurostimulator configured to treat urinary incontinence, sleep apnea, shoulder sublaxation, headache, etc.

Figure 1:
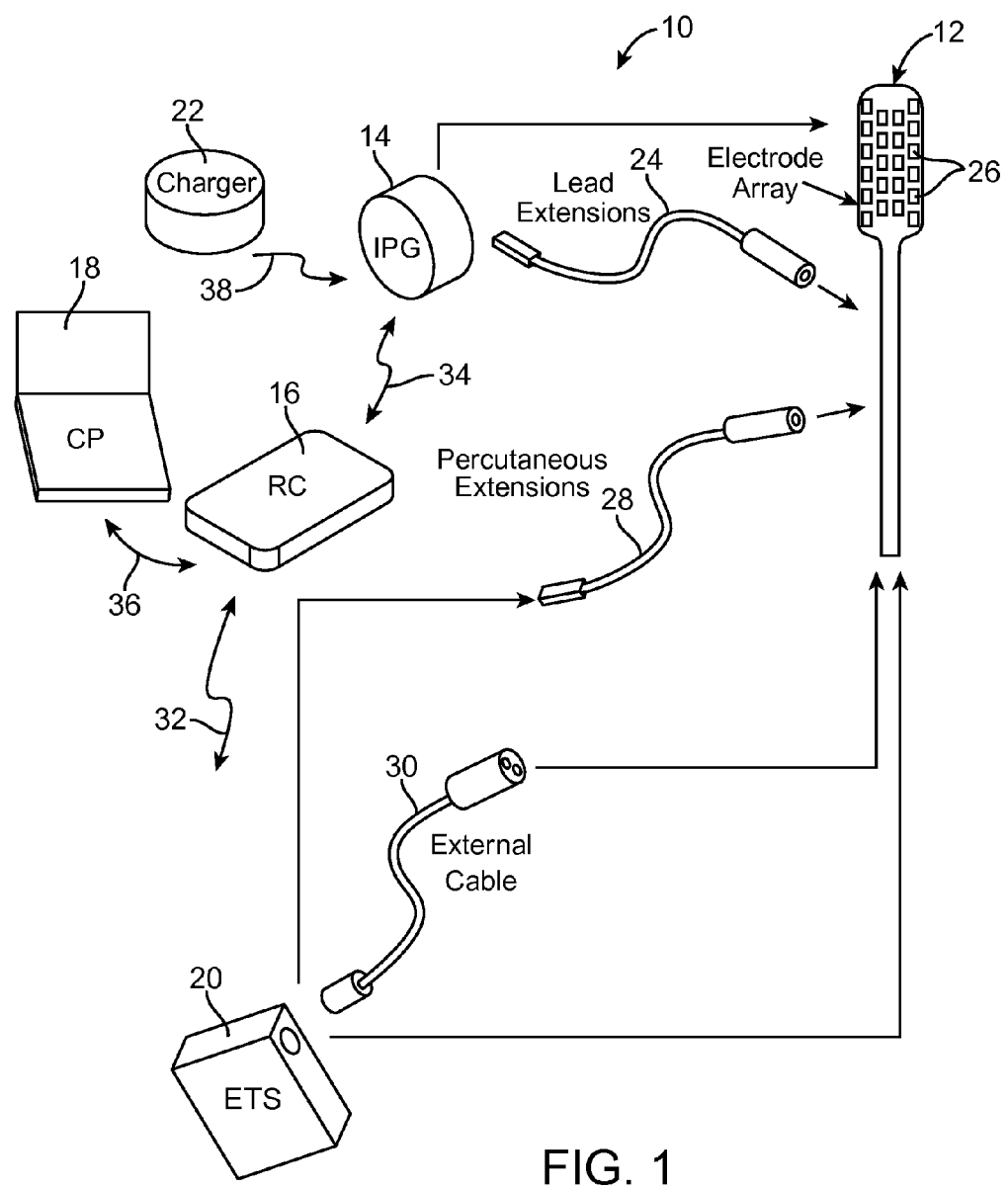
FIG. 1 is a plan view of a Spinal cord Stimulation (SCS) system constructed in accordance with one embodiment of the present inventions.

Turning first to FIG. 1, an exemplary SCS system 10 generally comprises at least one implantable neurostimulation lead 12, an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the neurostimulation lead 12, which carries a plurality of electrodes 26 arranged in an array. The neurostimulation lead 12 is illustrated as a surgical paddle lead in FIG. 1, although as will be described in further detail below, one or more percutaneous stimulation leads can be used in place of the surgical paddle lead 12. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
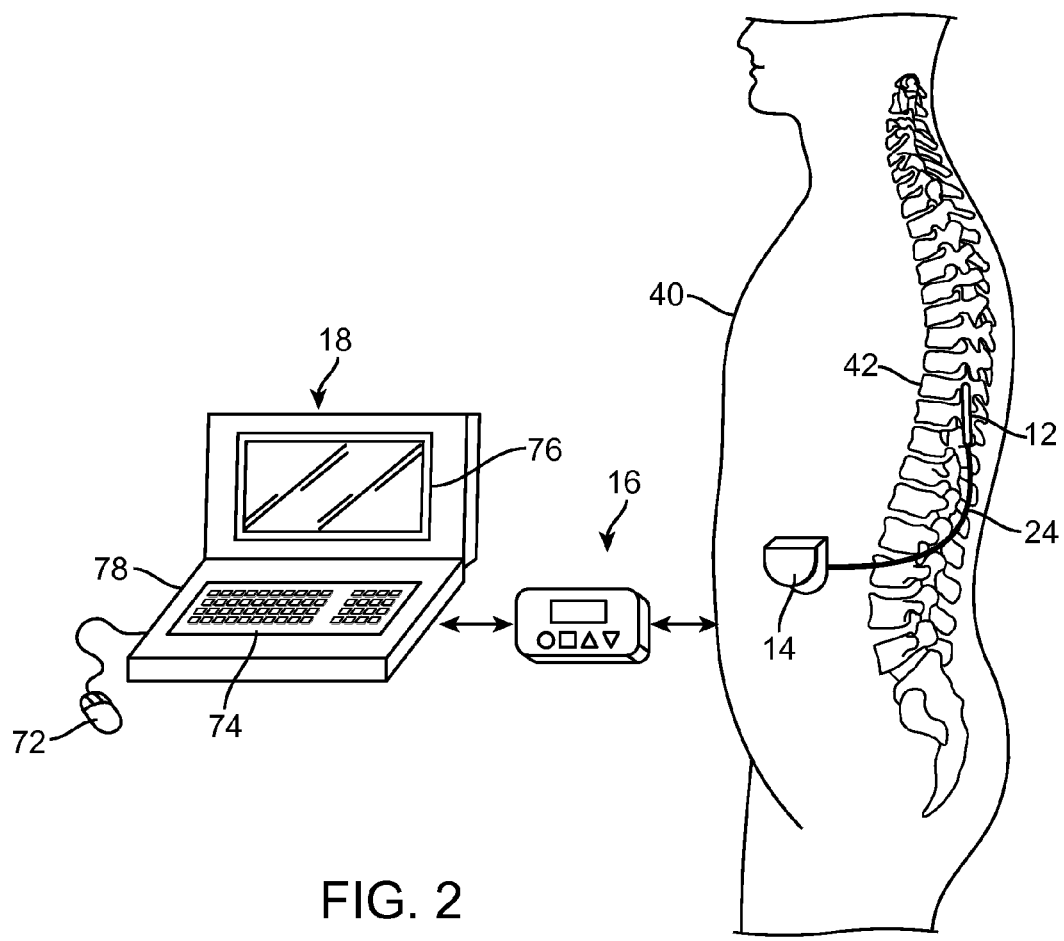
FIG. 2 is a perspective view of the arrangement of the SCS system of FIG. 1 with respect to a patient.

As shown in FIG. 2, the electrode lead 12 is implanted within the spinal column 42 of a patient 40. The preferred placement of the electrode lead 12 is adjacent, i.e., resting upon, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 3:
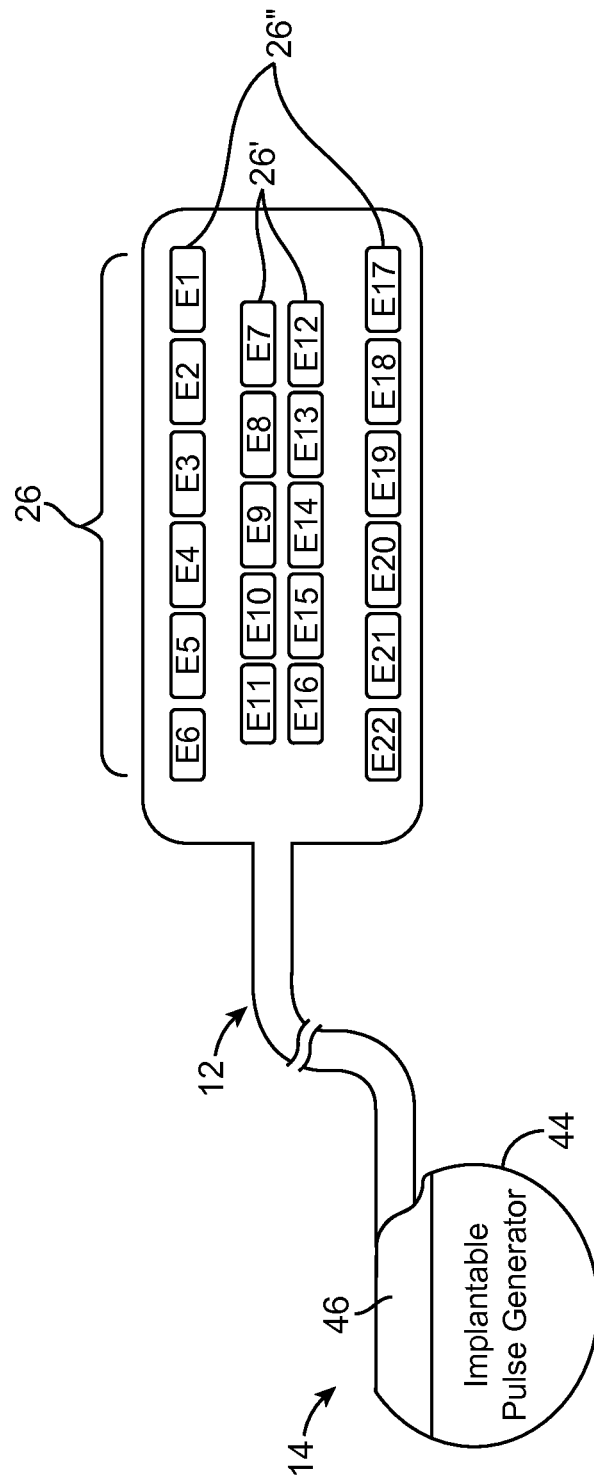
FIG. 3 is a profile view of an implantable pulse generator (IPG) and a surgical paddle lead used in the SCS system of FIG. 1.

Referring to FIG. 3, the IPG 14 comprises an outer case 44 for housing the electronic and other components (described in further detail below), and a connector 46 to which the proximal end of the neurostimulation lead 12 mates in a manner that electrically couples the electrodes 26 to the internal electronics (described in further detail below) within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

In the embodiment illustrated in FIG. 3, the neurostimulation lead 12 takes the form of a surgical paddle lead 12 on which the electrodes 26 (in this case, electrodes E1-E22) are carried. The electrodes 26 are arranged in a two-dimensional array in four columns along the axis of the neurostimulation lead 12. In the illustrated embodiment, the electrodes 26 are arranged in two inner columns of electrodes 26' (electrodes E7-E16), and two outer columns of electrodes 26" (electrodes E1-E6 and E17-E22) that flank and are longitudinally offset from the inner electrode columns. In other embodiments, the outer and inner electrode columns may not be longitudinally offset from each other. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," and U.S. Pat. No. 7,987,000, the disclosures of which are expressly incorporated herein by reference.

Figure 4:
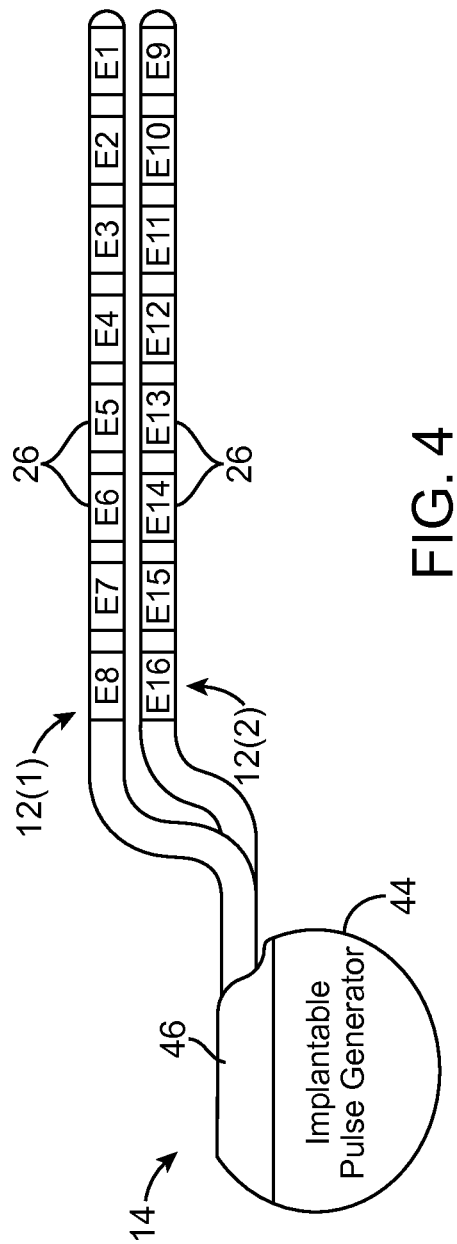
FIG. 4 is a profile view of an implantable pulse generator (IPG) and percutaneous leads used in the SCS system of FIG. 1.

In an alternative embodiment illustrated in FIG. 4, the neurostimulation lead 12 takes the form of a percutaneous stimulation lead on which the electrodes 12 (in this case, electrodes E1-E8) are disposed as ring electrodes. Although only one percutaneous stimulation lead 12 is shown, multiple percutaneous stimulation leads (e.g., two), can be used with the SCS system 10. The actual number and shape of leads and electrodes will, of course, vary according to the intended application. Further details describing the construction and method of manufacturing percutaneous stimulation leads are disclosed in U.S. Pat. Nos. 8,019,439 and 7,650,184, the disclosures of which are expressly incorporated herein by reference.

As will be described in further detail below, the IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation phase and an anodic (positive) recharge phase that is generated after the stimulation phase to prevent direct current charge transfer through the tissue, thereby avoiding electrode degradation and cell trauma. That is, charge is delivered through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
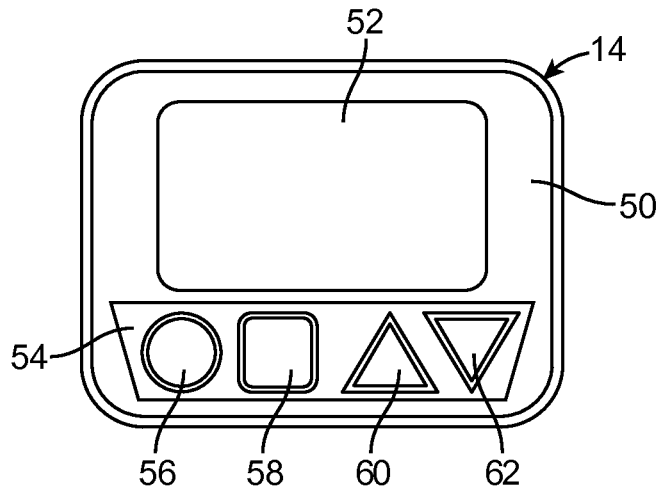
FIG. 5 is front view of a remote control (RC) used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touch screen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
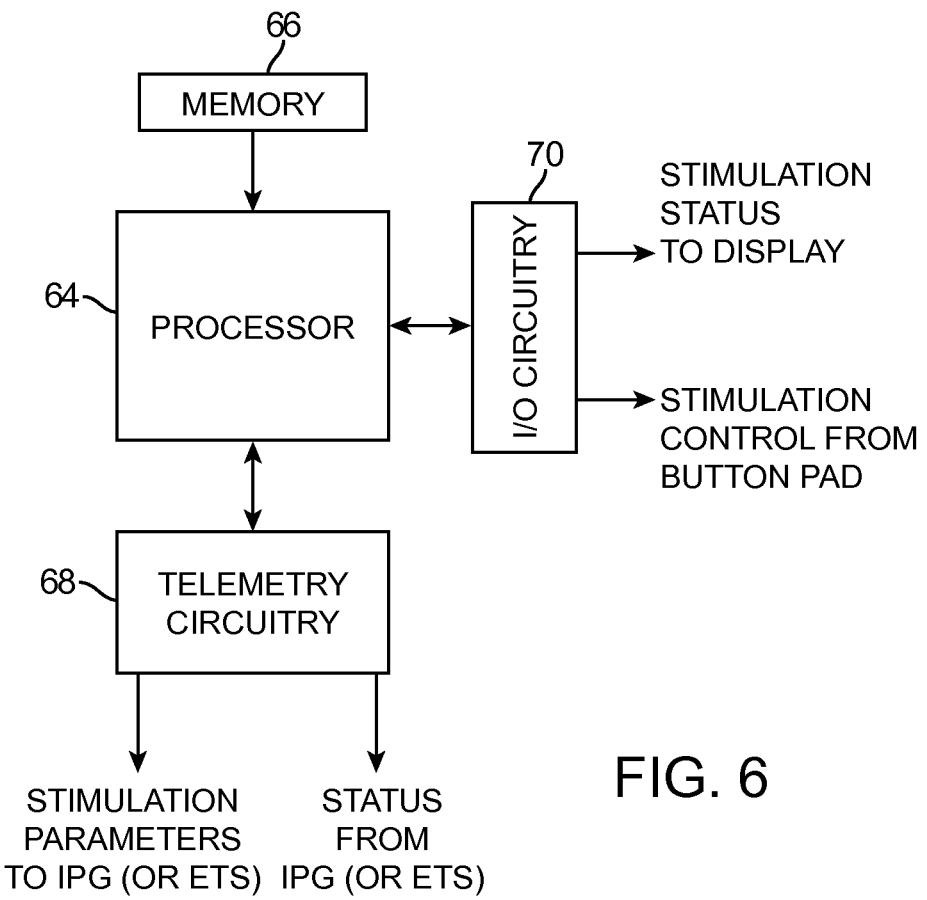
FIG. 6 is a block diagram of the internal components of the RC of FIG. 4.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 5). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

To allow the user to perform these functions, the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch.

Figure 7:
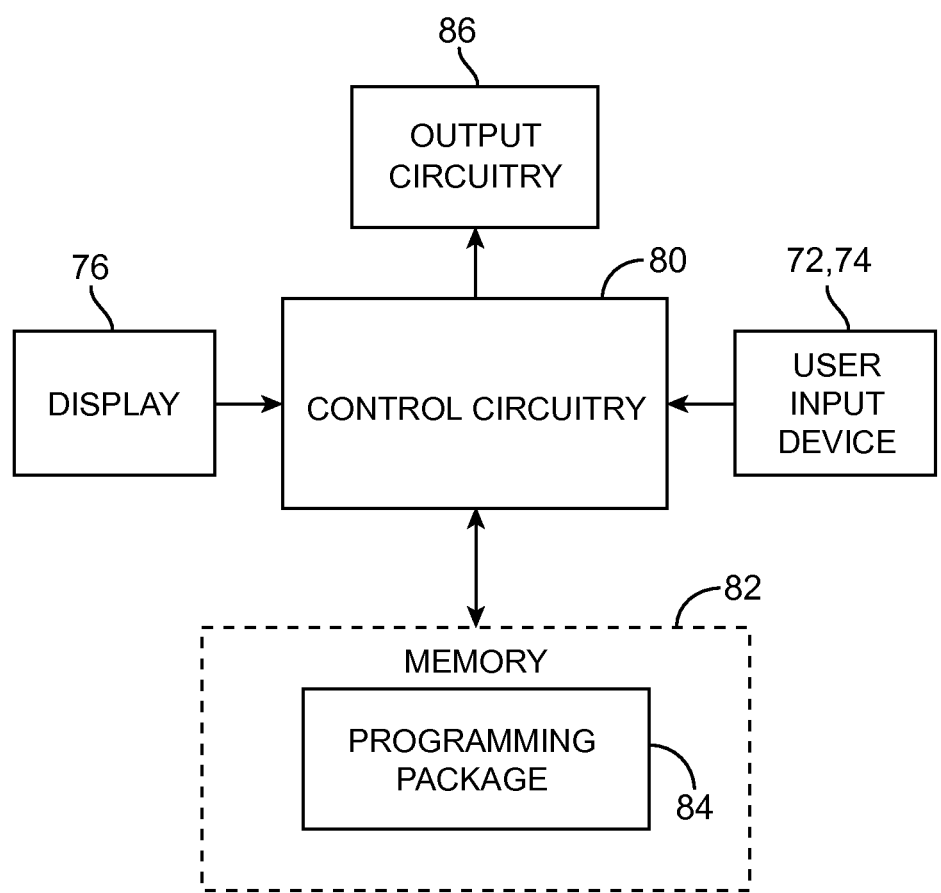
FIG. 7 is a block diagram of the internal components of a clinician's programmer (CP) used in the SCS system of FIG. 1.

As shown in FIG. 7, the CP 18 further includes a control circuitry 80 (e.g., a central processor unit (CPU)) and memory 82 that stores a stimulation programming package 84, which can be executed by the control circuitry 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the control circuitry 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a user interface that conveniently allows a user to program the IPG 14 in a manner that emulates an ideal multipole, such as a bipole or tripole, much like in the manner described in U.S. Pat. No. 8,412,345, which was previously incorporated herein by reference. However, in this case, the programming package 84 provides a series of different ideal multipole configurations that can be used to steer electrical current relative to the electrodes 12 in response to directional control signals generated in response to manipulation of a directional programming device, such as one or more of the directional programming devices described above.

Figure 8:
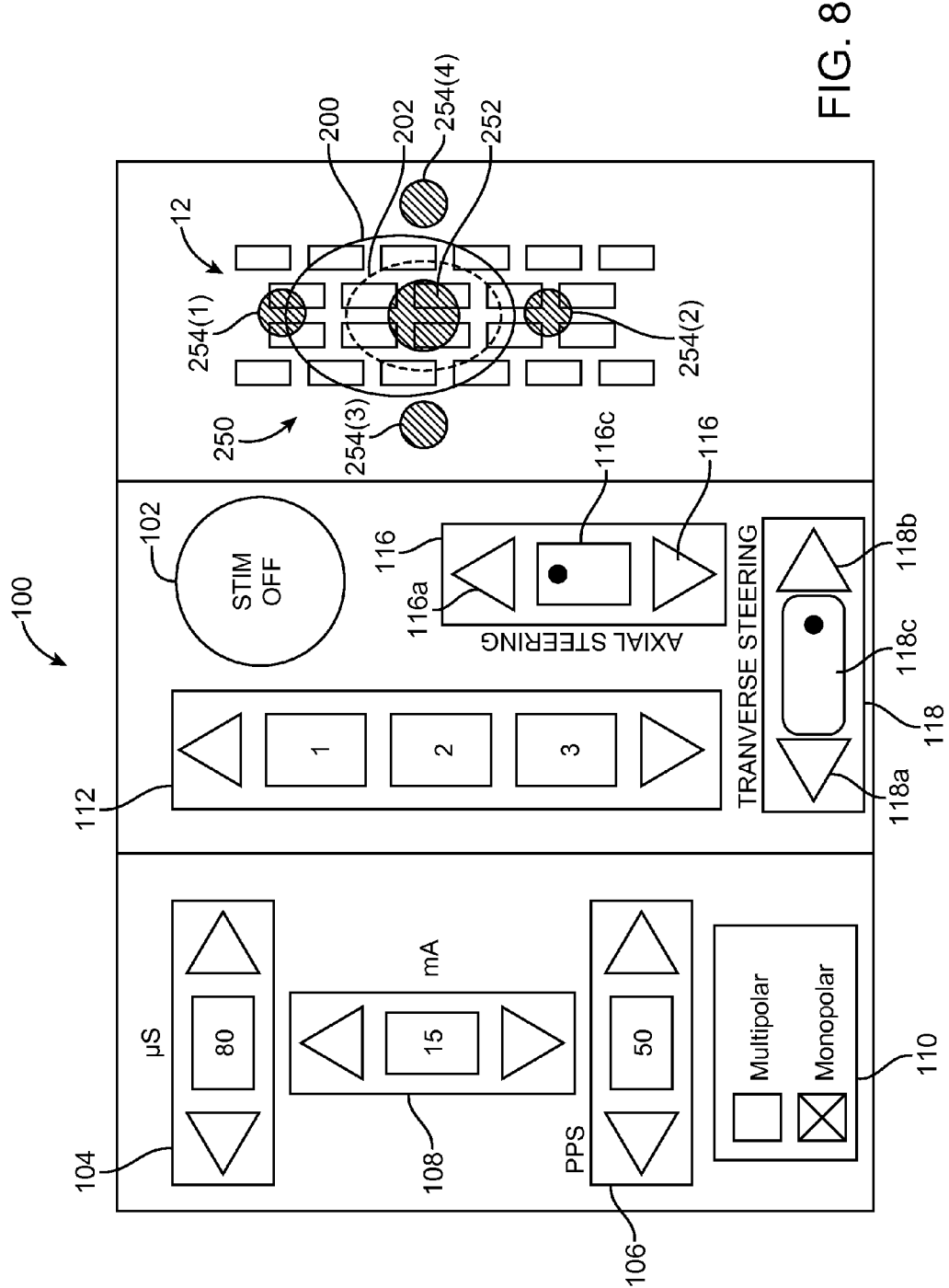
FIG. 8 is a plan view of a user interface of the CP of FIG. 7 for programming the IPG of FIG. 3.

With reference first to FIG. 8, a programming screen 100 can be generated by the CP 16. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements.

The programming screen 100 also includes a set of axial steering control elements 116 and a set of transverse steering control elements 118. In the illustrated embodiments, the control elements 116, 118, as well as the other control elements discussed herein, are implemented as a graphical icon that can be clicked with a mouse or touched with a finger in the case of a touchscreen. Alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements.

When any of the axial steering control elements 116 is actuated, control signals are generated in response to which the control circuitry 80 is configured for generating stimulation parameter sets designed to axially displace the locus of the electrical stimulation field (and thus, the volume of activation (VOA)) relative to the axis of the lead 12. Likewise, when any of the transverse steering control elements 118 is actuated, control signals are generated in response to which the control circuitry 80 is configured for generating stimulation parameter sets designed to transversely displace the locus of the electrical stimulation field (and thus, the VOA) relative to the axis of the lead 12.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the control circuitry 80 is configured for generating the plurality of stimulation parameter sets. The output telemetry circuitry 86 is configured for transmitting these stimulation parameters sets to the IPG 14.

Preferably, the control signals that are generated in response to the actuation of the control elements 116, 118 or the alternative control elements are directional, meaning that the locus of the electrical stimulation field will be displaced in a defined direction in response to a continual actuation of a single control element irrespective of the current position of the locus electrical stimulation field locus. As will be described in further detail below, the control circuitry 80, in response to the actuation of the control elements 116, 118, first defines a series of ideal multipoles, and computationally determines the stimulation parameters, including the fractional ized current values on each of the electrodes, in a manner that emulates these ideal multipoles.

Each of the sets of control elements 116, 118 takes the form of a double arrow (i.e., two oppositely pointing control element arrows) that can be actuated to modify the electrical stimulation field depending on the mode of operation. For example, an upper arrow control element 116a can be clicked to axially displace (i.e., along the axis of the lead 12) the locus of the electrical stimulation field in the proximal direction; a lower arrow control element 116b can be clicked to axially displace (i.e., along the axis of the lead 12) the locus of the electrical stimulation field in the distal direction; a left arrow control element 118a can be clicked to transversely displace (i.e., perpendicular to the axis of the lead 12) the locus of the electrical stimulation field in the leftward direction; and a right arrow control element 118b can be clicked to transversely displace (i.e., perpendicular to the axis of the lead 12) the locus of the electrical stimulation field in the rightward direction. The control elements 116, 118 also include indicators 116c, 118c for displaying an indication of the locus of the electrical stimulation field relative to the lead 12. In particular, an indicator 116c displays a dot representative of the axial displacement of the electrical stimulation field locus, and an indicator 118c displays a dot representative of the transverse displacement of the electrical stimulation field locus.

Although the programming screen 100 illustrates a surgical paddle lead, it should be appreciated that the programming screen 100 may illustrate one or more percutaneous to either arrange the electrodes 12 in an axial direction (in the case of a single neurostimulation lead) and allowing the electrical current to be steering in an axial direction, or arranging the electrodes 12 in two dimensions (in the case of multiple neurostimulation leads), thereby arranging the electrodes in two dimensions and allowing the electrical current to be steered in two dimensions much like the surgical paddle lead. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional patent application Ser. No. 61/374,879), in which case, the electrical current can be steering in three-dimensions.

The programming screen 100 displays a two-dimensional graphical rendering of the electrode array 26 relative to a graphical representation of the anatomical structure 200 that is preferably the stimulation target. Based on the current stimulation parameter set, the control circuitry 80 computes an estimate of a resulting volume of activation VOA 202, and generates display signals that prompt the monitor 76 to display a graphical representation of the VOA 202 with the graphical electrode array 26 and graphical anatomical structure 200. In the preferred embodiment, the graphical VOA 202 is superimposed over the graphical anatomical structure 200.

The programming screen 100 also displays a graphical rendering of an ideal multipole 250 that is manipulated by the control circuitry 80 relative to the electrode array 26. In one embodiment, the multipole 250 is a generalized multipole that defines five imaginary locations for a central ideal pole 252 and four surrounding ideal poles 254(1)-254(4) (collectively, 254). The generalized multipole 250 is defined with several sets of variable values that are stored in memory 82. These sets of variable values include a set of variable values defining the polarities of the central ideal pole 252 and surrounding ideal poles 254, a set of variable values defining a spatial relationship between the central ideal pole 252 and the electrode array 26, a set of variable values defining a spatial relationship between the surrounding ideal poles 254 and the central ideal pole 252, and a set of variable values defining relative intensities of the surrounding ideal poles 254.

Figures 9, 10, 11:
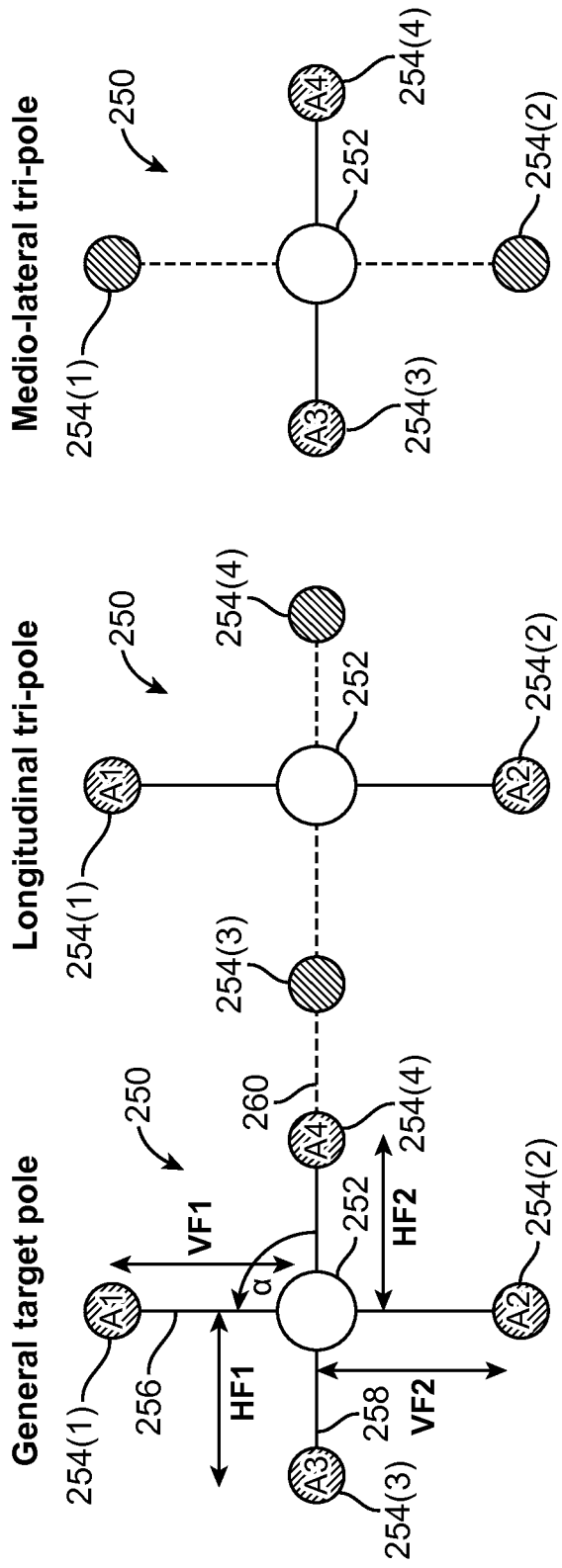
FIG. 9 is a plan view of generalized ideal multipole that can be used by the CP of FIG. 7 to define different ideal multipole configurations.
FIG. 10 is a plan view of a longitudinal ideal tripole configuration that can be derived from the generalized ideal multipole of FIG. 9.
FIG. 11 is a plan view of a transverse ideal tripole configuration that can be derived from the generalized ideal multipole of FIG. 9.

Referring further to FIG. 9, in accordance with typical SCS regimens, which assume that neurons are stimulated by negatively polarized current, the set of variable values defining the polarities in the illustrated embodiment, defines the polarity of the central ideal pole 252 as being a cathode ("−") and the polarities of the surrounding ideal poles 254 as being anodes ("+"). In alternative embodiments, the central ideal pole 252 may be defined as an anode ("+") and the polarities of the surrounding ideal poles 254 may be defined as cathodes ("−"). Alternatively, rather than having a set of variable values that define the polarities of the ideal poles, the polarities of the ideal poles may be pre-defined in a fixed manner, such that they cannot be varied.

In the illustrated embodiment, the spatial relationship between the central ideal pole 252 and the electrode array 26 is a rectilinear position (e.g., an x-y position in a two-dimensional coordinate system, or an x-y-z position in a three-dimensional coordinate system). In alternative embodiments, the spatial relationship between the central ideal pole 252 and the electrode array 26 may be a position in a polar coordinate system, cylindrical coordinate system, or spherical coordinate system. The spatial relationship between the central ideal pole 252 and the electrode array 26 may be stored as absolute coordinate positions for both the central ideal pole 252 and the electrode array 26, or may be stored as a relative coordinate position between the central ideal pole 252 and the electrode array 26. The spatial relationship between the central ideal pole 252 and the electrode array 26 may be determined relative to a reference point in the electrode array 26, e.g., a designated electrode.

In the illustrated embodiment, the spatial relationship between the surrounding ideal poles 254 and the central ideal pole 252 comprises an absolute distance (referred to as "focus") between each of the surrounding ideal poles 254 and the central ideal pole 252. In particular, the spatial relationship between the first ideal pole 254(1) and the central ideal pole 252 is defined by a vertical focus VF1, the spatial relationship between the second ideal pole 254(2) and the central ideal pole 252 is defined by a vertical focus VF2, the spatial relationship between the third ideal pole 254(3) and the central ideal pole 252 is defined by a horizontal focus HF1, and the spatial relationship between the fourth ideal pole 254(4) and the central ideal pole 252 is defined by a horizontal focus HF2.

In the illustrated embodiment, the relative intensities A1-A4 of the surrounding ideal poles 254 are defined using fractionalized values. For example, each of the surrounding ideal poles 254 may have an intensity of 25%. Notably, if a specific ideal pole 254 is turned on (or activated), it will have a non-zero intensity value, and if a specific ideal pole 254 is turned off (not activated), it will have a zero intensity value. Thus, if the relative intensities A1, A2 are non-zero (ideal poles 254(1), 254(2) activated), and the relative intensities A3, A4 are zero (ideal poles 254(3), 254(4) not activated), a longitudinal tripole configuration (rostro-caudal in the case of SCS) can be formed from the generalized ideal multipole 250, as shown in FIG. 10. In contrast, if the relative intensities A3, A4 are non-zero (ideal poles 254(3), 254(4) activated), and the relative intensities A1, A2 are zero (ideal poles 254(1), 254(2) not activated), a transverse tripole configuration (medio-lateral in the case of SCS) can be formed from the generalized ideal multipole 250, as shown in FIG. 11.

The ideal poles 254(1) and 254(2) and the central ideal pole 252 are aligned along a first axis 256 along which the absolute distances for the ideal poles 254(1) and 254(2) are defined, and the ideal poles 254(3) and 254(4) and the central ideal pole 252 are aligned along a second axis 258 along which the absolute distances for the ideal poles 254(3) and 254(4) are defined. In this case, a set of variable values defining an angle between one or both of the axes 256, 258 and a reference axis 260 may be stored in memory 82.

Figure 12:
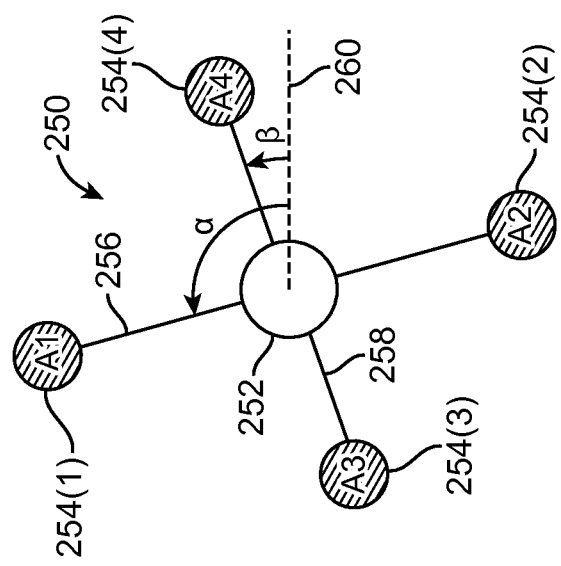
FIG. 12 is a plan view of a rotated ideal tripole configuration that can be derived from the generalized ideal multipole of FIG. 9.

In the illustrated embodiment, the reference axis 260 is an axis that is transverse to the longitudinal axis of the lead 12. For example, as shown in FIG. 9, the angle α between the axis 256 and the reference axis 260 is defined to be 90 degrees, essentially aligning the ideal multipole 250 with the electrode array 26. As shown in FIG. 12, the angle α between the axis 256 and the reference axis 260 is defined to be 120 degrees, such that the ideal multipole 250 is rotationally offset from the electrode array 26.

Figure 13:
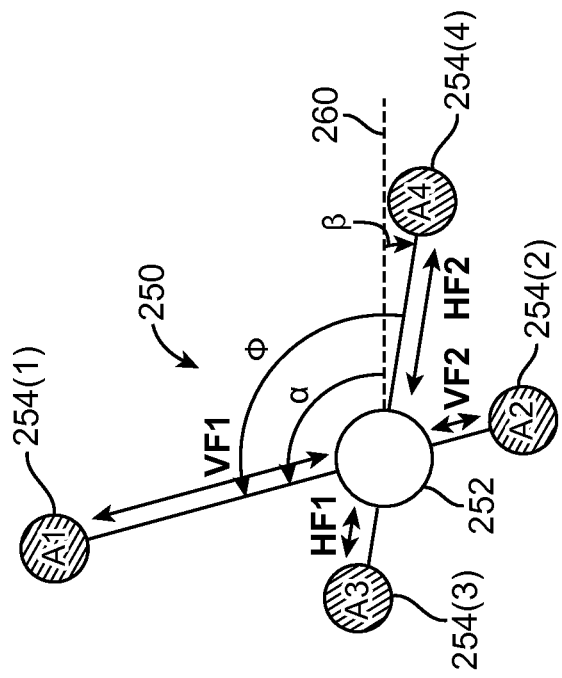
FIG. 13 is a plan view of an asymmetric ideal tripole configuration that can be derived from the generalized ideal multipole of FIG. 9.

If the relative angle between the axes 256, 258 is fixed (i.e., the axes 256, 258 cannot be rotated relative to each other), only one angle (e.g., the angle between the axis 256 and the reference axis 260) needs to be used. This may, e.g., be the case when the axes 256, 258 are always assumed to be orthogonal to each other, as shown in FIGS. 9 and 12. However, in alternative embodiments, the axes 256, 258 may be rotated relative to each other, in which case, two angles need to be defined. For example, as shown in FIG. 13, the angle α between the axis 256 and the reference axis 260 is defined to be 120 degrees, and the angle β between the axis 258 and the reference axis 260 is defined to be −15 degrees. In this case, the axes 256, 258 are non-orthogonal to each other. Alternatively, rather than defining the angles for both axes 256, 258 relative to the reference axis 260, the angle of one of the axes 256, 258 can be defined relative to the reference axis 260, and the angle of the other one of the axes 256, 256 can be defined relative to the one axes. For example, the angle α between the axis 256 and the reference axis 260 can be defined to be 120 degrees, and the angle ϕ between the axes 256, 258 can be defined to be 135 degrees.

In the preferred embodiment, the vertical focuses VF1, VF2 for the respective ideal poles 254(1), 254(2), and the horizontal HF1, HF2 for the respective ideal poles 254(3), 254(4), are independently defined. For example, although in the FIG. 9 embodiment, the vertical focuses VF1, VF2 are equal (symmetrical) and the horizontal focuses HF1, HF2 are equal (symmetric), in the FIG. 13 embodiment, the vertical focuses VF1, VF2 are not equal (VF1 is greater than VF2) (asymmetric), and the horizontal focuses HF1, HF2 are not equal (HF1 is less than HF2)(asymmetric).

The control circuitry 80 is configured for modifying at least one of the sets of values that define the ideal multipole 250 in response to the directional control signals generated by the user interface. For example, the control circuitry 80 may modify the polarities of the central ideal pole 252 and surrounding ideal poles 254, the rectilinear position of the central ideal pole 252 relative to the electrode array 26, the vertical focuses VF1, VF2 and horizontal focuses HF1, HF2, the fractionalized values A1-A4 of the surrounding ideal poles 254, and/or any of the angles α, β, ϕ. In an optional embodiment, the control circuitry 80 may modify one of the sets of values that define the ideal multipole 250 as a function of an automated sequence (e.g., the sets of values are modified every second), as a function of an electrode boundary (e.g., the ideal multipole 250 must remain within a certain electrode region), or as a function of a particular electrode position (e.g., one of the poles of the ideal multipole 250 must be affixed to a particular electrode).

The control circuitry 80 is further configured for generating, based on the modification, stimulation parameter values defining relative amplitude values for the respective electrodes 12 to emulate the selected poles of the ideal multipole 250, and instructing the IPG 14 to convey electrical energy to the electrode array 26 in accordance with the stimulation parameter values. Further details discussing the computation of relative electrode amplitude values to emulate ideal multipoles are disclosed in U.S. Pat. No. 8,412,345, which was previously incorporated herein by reference.

Significantly, the control circuitry 80 may steer current in a particular direction by modifying the values defining the generalized ideal multipole 250 in response to the continual generation of the directional control signals, and instructing the IPG 14 to convey the electrical energy to the electrode array 26 in accordance with stimulation parameter values generated based on the modified values.

For example, the control circuitry 80 may be configured for sequentially defining a plurality of different ideal bipole/tripole configurations relative to electrode array 26 in response to the directional control signals.

Figure 14:
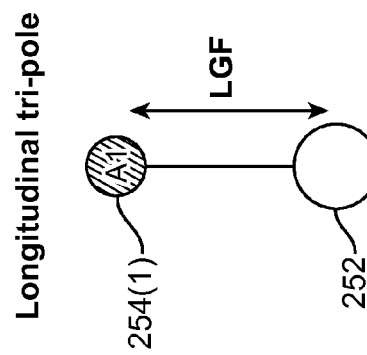
FIG. 14 is a plan view of a generalized ideal longitudinal tripole that can be used by the CP of FIG. 7 to define different ideal bipole/tripole configurations.

In one embodiment shown in FIG. 14, the control circuitry 80 utilizes a longitudinal tripole configuration having a central ideal cathode 252 and two flanking anodes 254(1) and 254(2) as a basis for defining the different ideal bipole/tripole configurations. The longitudinal tripole configuration can be derived from the generalized ideal multipole 250 by defining the polarization of the central ideal pole 252 to be a cathode and the polarizations of the surrounding ideal poles 254 to be anodes, defining the intensity values for the ideal poles 254(1) and 254(2) to be non-zero values, and defining the intensity values for the ideal poles 254(3) and 254(4) (not shown in FIG. 14) to be zero values. The characteristics of the basis longitudinal tripole configuration can be defined by a longitudinal focus (LGF) (equivalent to the vertical focus (VF1) of the generalized multipole 250), an upper anode percentage (UAP)(equivalent to the intensity value A1 of the generalized multipole 250), and the cathode position relative to the electrode array 26. The lower anode percentage can be computed in accordance with the equation A2=100−A1.

Figure 15:
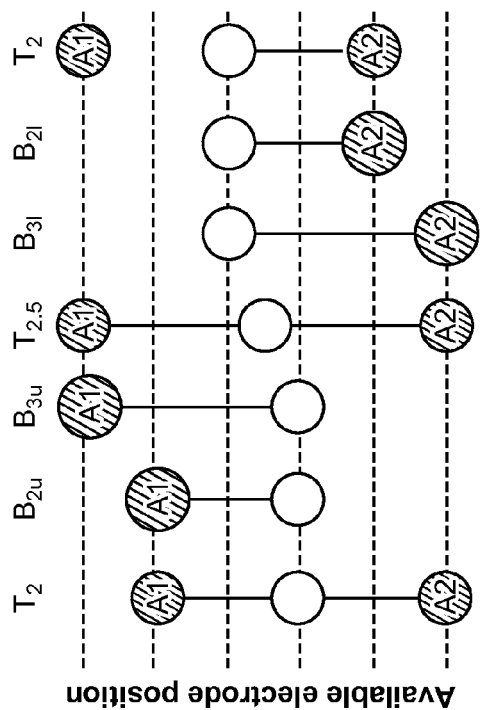
FIG. 15 is a sequence of different ideal bipole/tripole configurations that can be derived from the ideal longitudinal tripole of FIG. 14 to rostro-caudally displace a volume of activation.

The control circuitry 80 may sequentially define the different ideal bipole/tripole configurations in accordance with a weaving current steering technique. For example, a series of ideal bipole/tripole configurations are illustrated in FIG. 15 over a plurality of dashed lines representing available electrode positions in the electrode array 26. As shown, the individual poles of the ideal bipole/tripole configurations are generally maintained as much as possible over an available electrode position in order to emulate the ideal bipole/tripole configurations in the most energy efficient manner. In the illustrated embodiment, all of the ideal tripole configurations are symmetrical in that the ideal anodes are equally spaced from the central ideal cathode. Each illustrated bipole/tripole configuration has a designator indicating whether it is a tripole or bipole (T for tripole and B for bipole), a subscripted designator indicating the longitudinal focus (LGF) in terms of electrode separation, and, in the case of a bipole, a subscripted designator indicating the bipole is an upper bipole (u), meaning that the anode is above the cathode, or the bipole is a lower bipole (l), meaning that the anode is below the cathode.

In the embodiment illustrated in FIG. 15, the different ideal bipole/tripole configurations are sequentially defined in the following order: a narrow ideal tripole configuration ($T_2$), a narrow upper ideal bipole configuration ($B_{2u}$), a wide upper ideal bipole configuration ($B_{3u}$), a wide ideal tripole configuration ($T_{2.5}$), a wide lower ideal bipole configuration ($B_{3l}$), a narrow lower ideal bipole configuration ($B_{2l}$), and the narrow ideal tripole configuration ($T_2$). For purposes of this specification, the terms "narrow" and "wide," when used together to define an ideal bipole or an ideal tripole, are relative terms, and simply mean that the narrow bipole and/or narrow tripole have longitudinal focuses (LGFs) that are less than the longitudinal focuses (LGFs) of the wide bipole and/or wide tripole.

Figure 16:
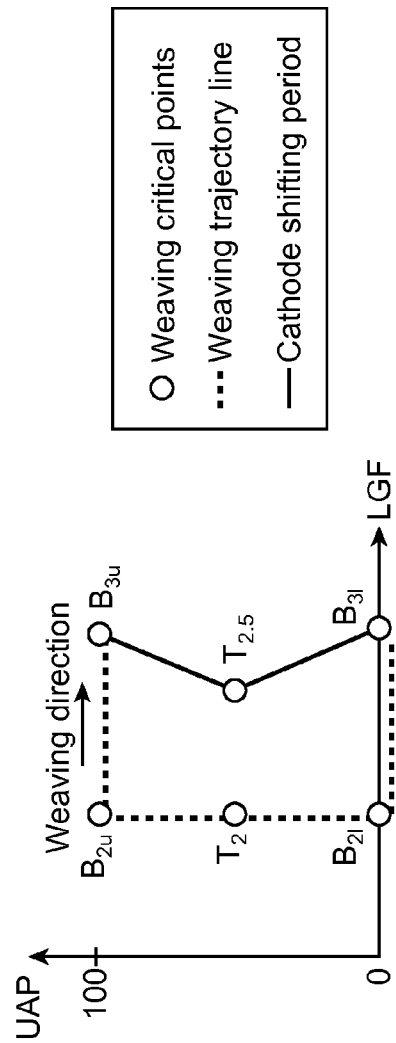
FIG. 16 is a plot illustrating a weaving space for the sequence of bipole/tripole configurations illustrated in FIG. 15.

The ideal bipole/tripole configurations illustrated in FIG. 15 may be considered critical points between which the cathode position and longitudinal focus (LGF) are incrementally changed by mapping the sequences in a "weave space," defined by the longitudinal focus (LGF) and the upper anode percentage (UAP). As best shown in FIG. 16, the sequence of ideal bipole/tripole configurations is defined by a trajectory line sequentially connecting the critical points (representing by circles) that provides a continuous change in the ideal bipole/tripole configurations.

As can be seen from FIG. 16, the sequence beginning with the narrow ideal tripole configuration ($T_2$) and ending with the narrow upper ideal bipole configuration ($B_{2u}$) incrementally increases the upper anode percentage (UAP) while maintaining the longitudinal focus (LGF). The sequence beginning with the narrow upper ideal bipole configuration ($B_{2u}$) and ending with the wide upper ideal bipole configuration ($B_{3u}$) maintains the upper anode percentage (UAP) while incrementally increasing the longitudinal focus (LGF). The sequence beginning with the wide upper ideal bipole configuration ($B_{3u}$) and ending with the wide ideal tripole configuration ($T_{2.5}$) incrementally decreases the upper anode percentage (UAP) while incrementally decreasing the longitudinal focus (LGF). The sequence beginning with the wide ideal tripole configuration ($T_{2.5}$) and ending with the wide lower ideal bipole configuration ($B_{3l}$) incrementally decreases the upper anode percentage (UAP) while incrementally increasing the longitudinal focus (LGF). The sequence beginning with the wide lower ideal bipole configuration ($B_{3l}$) and ending with the narrow lower ideal bipole configuration ($B_{2l}$) maintains the upper anode percentage (UAP) while incrementally decreasing the longitudinal focus (LGF). The sequence beginning with the narrow lower ideal bipole configuration ($B_{2l}$) and ending with the narrow ideal tripole configuration ($T_2$) incrementally increases the upper anode percentage (UAP) while maintaining the longitudinal focus (LGF).

Notably, the above-mentioned sequence maintains the same position of the ideal cathode relative to the electrode array 26 while transitioning through different types of ideal bipole/tripole configurations between the narrow ideal tripole configuration ($T_2$) and the wide upper ideal bipole configuration ($B_{3u}$), incrementally changes the position of the ideal cathode relative to the electrode array 26 in one direction (in this case, upward) between the wide upper ideal bipole configuration ($B_{3u}$) and the wide lower ideal bipole configuration ($B_{3l}$), and the maintains the same position of the ideal cathode relative to the electrode array 26 while transitioning through different types of ideal bipole/tripole configurations between the wide lower ideal bipole configuration ($B_{3l}$) and the narrow ideal tripole configuration ($T_2$).

The sequence illustrated in FIG. 15 can be repeatedly cycled through, with the effect being that the ideal cathode is shifted upward by one electrode per each cycle. When electrical energy is conveyed to the electrode array 26 in accordance with stimulation parameter sets computed to emulate the sequence of bipolar/tripole configurations, a volume of activation (VOA) will be incrementally displaced along the tissue of the patient in concordance with the incremental displacement of the ideal cathode. If each ideal bipole/tripole configuration is generally aligned along the spinal cord of the patient, the VOA will be rostro-caudally displaced along the spinal cord of the patient.

Figure 18:
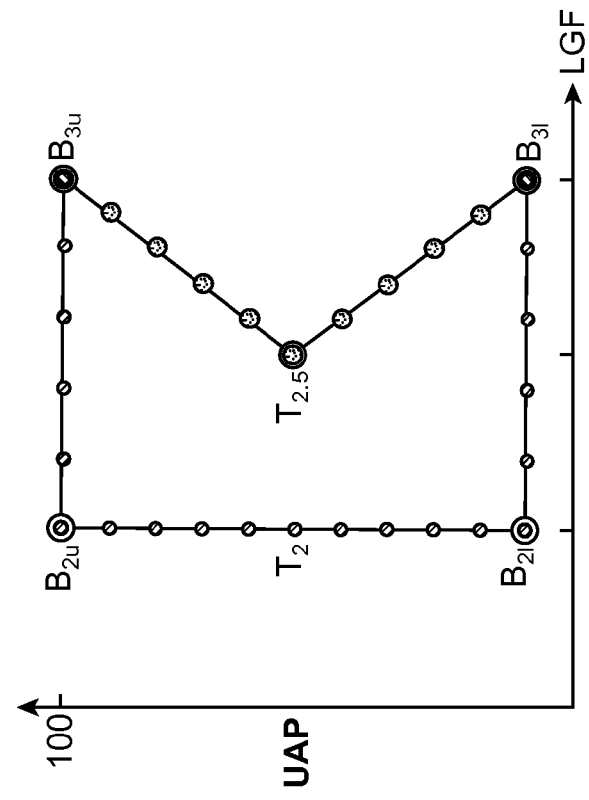
FIG. 18 is a plot illustrating the weaving space of FIG. 16, particularly showing the coarse resolution incremental steps between the ideal bipole/tripole configurations.
Figure 17:
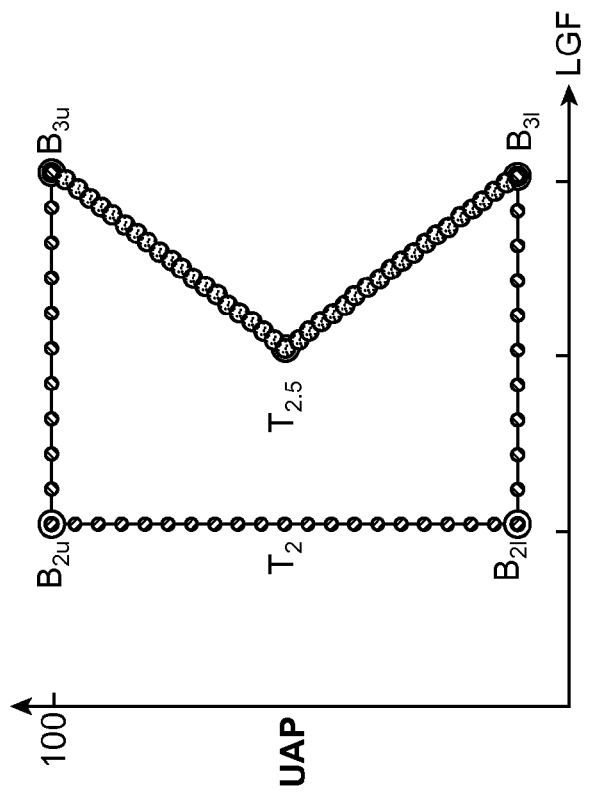
FIG. 17 is a plot illustrating the weaving space of FIG. 16, particularly showing the fine resolution incremental steps between the ideal bipole/tripole configurations.

Notably, different step sizes may be used transition between the ideal bipole/tripole configurations. For example, as shown in FIG. 17, a fine resolution (10 steps per critical point transition) are used to transition between the critical points where the cathode is not being shifted, and an even finer resolution (20 steps per critical point transition) are used to transition between the critical points where the cathode is being shifted. As shown in FIG. 18, a coarse resolution (5 steps per critical point transition) is used to transition between all of the critical points.

It should be appreciated that the different ideal bipole/tripole configurations may be sequentially defined in a different order and shift the cathode using different ones of the bipole/tripole configurations as compared to the sequence illustrated in FIG. 15. For example, as shown in FIG. 19, the different ideal bipole/tripole configurations may be defined in the following order: a narrow upper ideal bipole configuration ($B_{2u}$), a wide upper ideal bipole configuration ($B_{3u}$), a wide ideal tripole configuration ($T_3$), a wide lower ideal bipole configuration ($B_{3l}$), a narrow lower ideal bipole configuration ($B_{2l}$), a narrow ideal tripole configuration ($T_{2.5}$), and the narrow upper ideal bipole configuration ($B_{2u}$).

Figure 20:
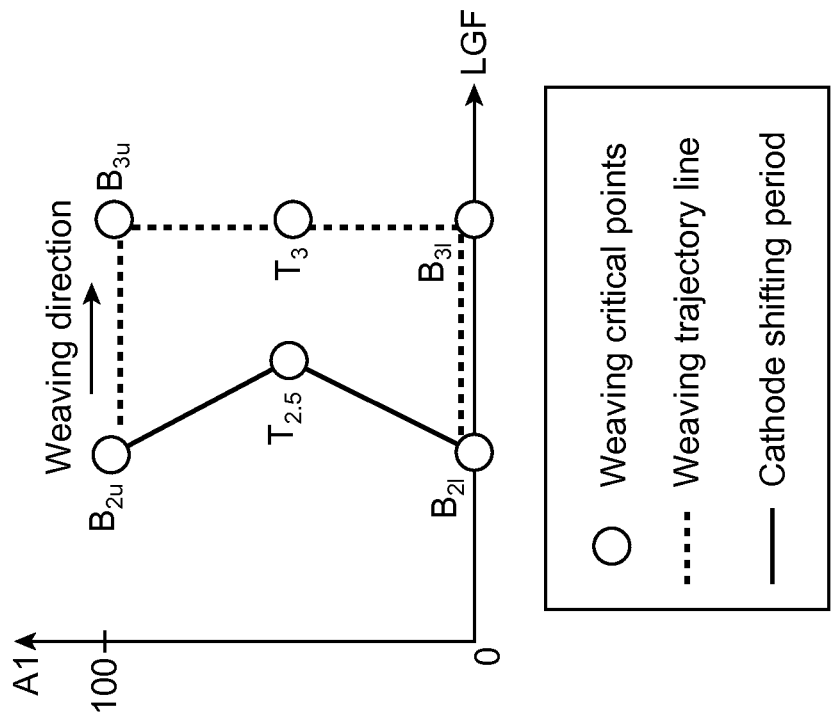
FIG. 20 is a plot illustrating a weaving space for the sequence of ideal bipole/tripole configurations illustrated in FIG. 19.

As best shown in FIG. 20, the sequence of ideal bipole/tripole configurations is defined by a trajectory line sequentially connecting the critical points (representing by circles). As can be seen, the sequence beginning with the narrow upper ideal bipole configuration ($B_{2u}$) and ending with the wide upper ideal bipole configuration ($B_{3u}$) maintains the upper anode percentage (UAP) while incrementally increasing the longitudinal focus (LGF). The sequence beginning with the wide upper ideal bipole configuration ($B_{3u}$) and ending with the wide ideal tripole configuration ($T_3$) incrementally decreases the upper anode percentage (UAP) while maintaining the longitudinal focus (LGF). The sequence beginning with the wide ideal tripole configuration ($T_3$) and ending with the wide lower bipole configuration ($B_{3l}$) incrementally decreases the upper anode percentage (UAP) while maintaining the longitudinal focus (LGF). The sequence beginning with the wide lower ideal bipole configuration ($B_{3l}$) and ending with the narrow lower ideal bipole configuration ($B_{2l}$) maintains the upper anode percentage (UAP) while incrementally decreasing the longitudinal focus (LGF). The sequence beginning with the narrow lower ideal bipole configuration ($B_{2l}$) and ending with the narrow ideal tripole configuration ($T_{2.5}$) incrementally increases the upper anode percentage (UAP) while incrementally increasing the longitudinal focus (LGF). The sequence beginning with the narrow ideal tripole configuration ($T_{2.5}$) and ending with the narrow upper ideal bipole configuration ($B_{2u}$) incrementally increases the upper anode percentage (UAP) while incrementally decreasing the longitudinal focus (LGF).

Notably, the above-mentioned sequence maintains the same position of the ideal cathode relative to the electrode array 26 while transitioning through different types of ideal bipole/tripole configurations between the narrow upper ideal bipole configuration ($B_{2u}$) and the narrow lower ideal bipole configuration ($B_{2l}$), and incrementally changes the position of the ideal cathode relative to the electrode array 26 in one direction (in this case, upward) between the narrow lower ideal bipole configuration ($B_{2l}$) and the narrow upper ideal bipole configuration ($B_{2u}$).

Figure 19:
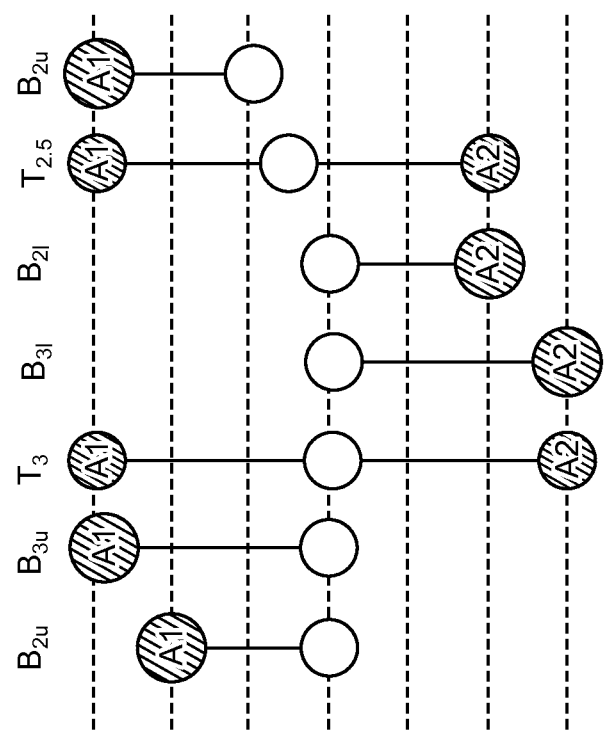
FIG. 19 is another sequence of different ideal bipole/tripole configurations that can be derived from the ideal longitudinal tripole of FIG. 14 to rostro-caudally displace a volume of activation.

The sequence illustrated in FIG. 19 can be repeatedly cycled through, with the effect being that the ideal cathode is shifted upward by one electrode per each cycle. As discussed above with respect to FIG. 15, if each of ideal bipole/tripole configuration is generally aligned along the spinal cord of the patient, when electrical energy is conveyed to the electrode array 26 in accordance with stimulation parameter sets computed to emulate the sequence of bipolar/tripole configurations, a volume of activation (VOA) will be incrementally rostro-caudally displaced along the spinal cord of the patient in concordance with the incremental displacement of the ideal cathode.

Although the cathode and anodes of the tripole configurations are aligned along an axis, as illustrated in FIGS. 15 and 19, it should be appreciated that the cathode and anodes may be misaligned along the axis. For example, in the manner illustrated in FIG. 13, the control circuitry 80 may define the angles α and β in a manner that the ideal poles 254(1) and 254(2) and central ideal pole 252 are misaligned along the axis 256.

Rather than sequentially defining different ideal bipole/tripole configurations that are aligned in the same direction, in response to the directional control signals, the control circuitry 80 may be configured for sequentially defining a plurality of different ideal multipole configurations, some of which may be orthogonal to each other.

Figure 21:
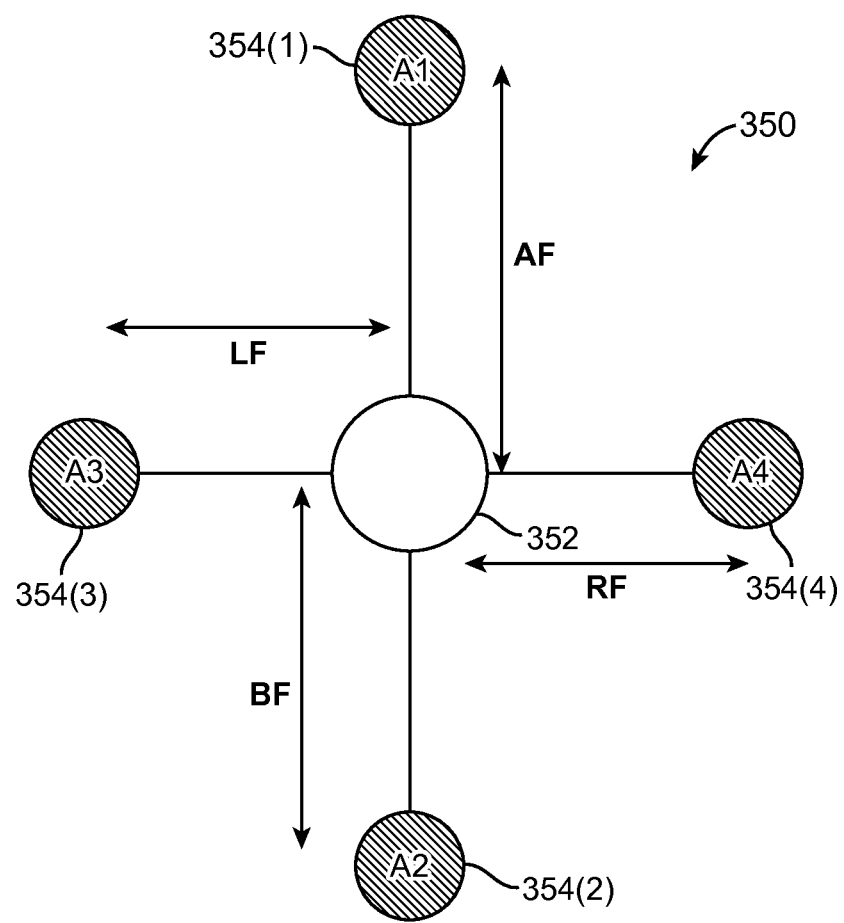
FIG. 21 is a plan view of a generalized ideal multipole that can be used by the CP of FIG. 7 to define different ideal multipole configurations.

In one embodiment shown in FIG. 21, the control circuitry 80 utilizes a generalized ideal multipole 300 having a central ideal cathode 352 and four surrounding ideal anodes 354 as a basis for defining the orthogonal multipole configurations. The generalized ideal multipole 300 can be derived from the generalized ideal multipole 250 by defining the polarization of the central ideal pole 252 to be a cathode and the polarizations of the surrounding ideal poles 254 to be anodes. The vertical focuses VF1, VF2 of the generalized ideal multipole 250 have been respectively replaced with an above anode focus AF and a below anode focus BF, and the horizontal focuses HF1, HF2 of the generalized ideal multipole 250 have been respectively replaced with a left anode focus LF and a right anode focus RF.

Figure 22A:
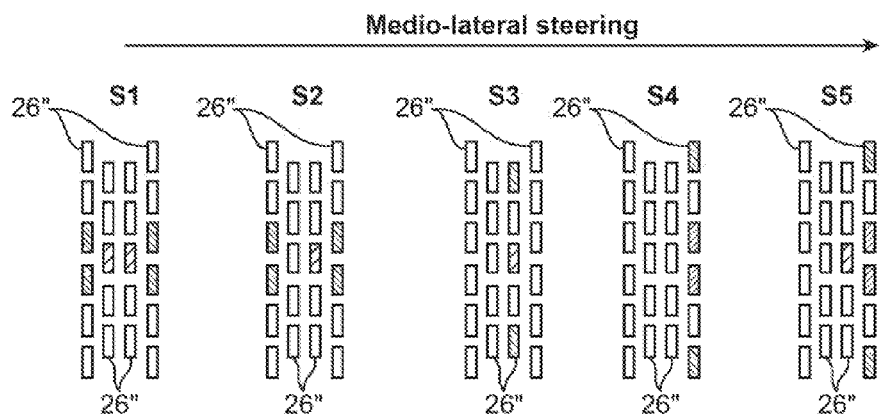
FIG. 22a is a sequence of electrode configurations that can be defined by the CP of FIG. 7 to medio-laterally displace a volume of activation.
Figure 22B:
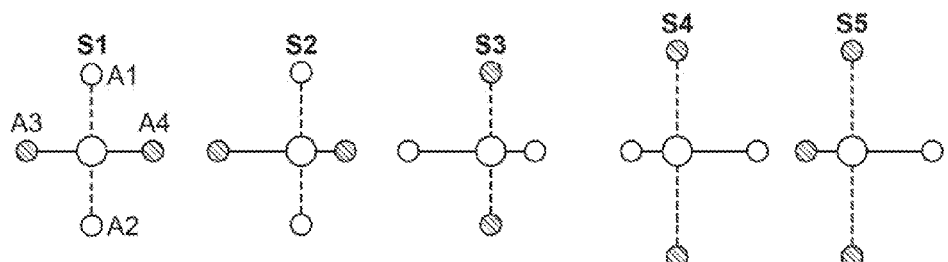
FIG. 22b is a sequence of ideal multipole configurations that can be derived from the generalized ideal multipole of FIG. 21 to medio-laterally displace a volume of activation.
Figure 22C:
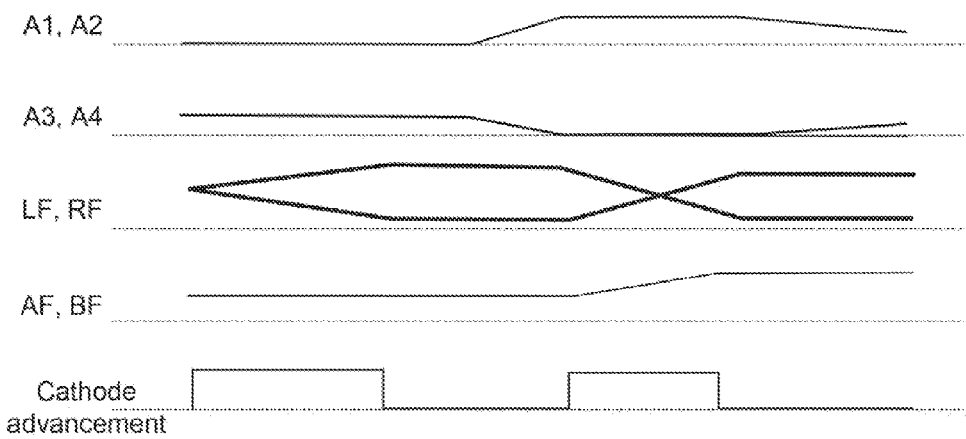
FIG. 22c is plot of the different parameter values used to transition between the ideal multipole configurations of FIG. 22b.

With reference to FIGS. 22a-22c, a series of active electrode combinations using the electrode array 26 of FIG. 3 can be generated to shift a volume of activation (VOA) from a medial to a lateral location. As will be described in further detail below, the ideal multipoles can be generated to match the actual sequence of active electrode combinations.

The sequence of active electrode combinations may begin with a transverse tripole electrode arrangement S1 created by activating the middle row in the inner electrode columns 26' (electrodes E9, E14) as cathodes, and activating the two flanking electrodes in the left outer column 26" (electrodes E3, E4) and the two flanking electrodes in the right outer column 26" (electrodes E19, E20) as anodes, thereby creating a medial-lateral electrical field that effectively places the VOA in a medial position relative to the electrode array 26. This transverse tripole arrangement provides high selectivity for DC nerve fibers over DR nerve fibers.

Another transverse tripole electrode arrangement S2 is created by using the same transverse tripole electrode arrangement S1, but deactivating the electrode in the left inner electrode column 26' (electrode E9), thereby creating a medial-lateral electrical field that laterally shifts the resulting VOA to the right from the medial position.

A narrow longitudinal tripole electrode arrangement S3 is created by activating the middle electrode in the right inner electrode column 26' (electrode E14) as a cathode, and activating two flanking electrodes in the right inner electrode column 26' (electrodes E12, E16) as anodes, thereby creating a rostral-caudal electrical field that shifts the resulting VOA further to the right.

A wide longitudinal tripole electrode arrangement S4 is created by activating the middle two electrodes in the right outer electrode column 26' (electrodes E19, E20), and activating two flanking electrodes in the right outer electrode column 26' (electrodes E17, E22), thereby creating a rostral-caudal electrical field that shifts the resulting VOA all the way to the right.

A quadpole electrode arrangement S5 is created by using the longitudinal tripole electrode arrangement S4, but activating the middle electrode in the right inner electrode column 26' (electrode E14).

Notably, although displacement of the resulting VOA is shown to occur from the medial location to the right, it can be appreciated that the resulting VOA can be displaced from the medial location to the left As illustrated in FIG. 22b, the control circuitry 50 may sequentially define ideal multipole configurations that respectively match the active electrode arrangements illustrated in FIG. 22a. In particular, the control circuitry 50 may define the ideal multipole configurations in the following order: a first ideal tripole configuration S1 oriented in a first direction (transverse), a second ideal tripole configuration S2 oriented in the first direction (transverse), a third ideal tripole configuration S3 oriented in a second orthogonal direction (longitudinal), a fourth ideal tripole configuration S4 oriented in the second direction (longitudinal), and an ideal quadpole configuration S5.

Referring further to FIG. 22c, the control circuitry 50 defines the different multipole configurations in accordance with the anode intensities (A1-A4), anode focuses (AF, BF, LF, RF), and position of the central ideal cathode relative to the electrode array 26.

In particular, the first ideal tripole configuration S1 can be defined as a narrow, transverse, symmetrical ideal tripole configuration by setting the anode intensities A1, A2 to zero values, setting the anode intensities A3, A4 to non-zero values, and setting the left and right anode focuses LF, RF to relatively small equal values, and defining the relative position between the central ideal cathode and the electrode array 26, such that the central ideal cathode is transversely aligned between the two inner electrode columns 26'.

The second ideal tripole configuration S2 can be defined as a narrow, transverse, asymmetrical ideal tripole configuration by setting the anode intensities A1, A2 to zero values, setting the anode intensities A3, A4 to non-zero values, setting the left anode focus LF to be a relative large value, setting the right anode focus RF to be a relatively small value, and defining the relative position between the central ideal cathode and the electrode array 26, such that the central ideal cathode is transversely aligned with the right inner electrode column 26'.

The third ideal tripole configuration S3 can be defined as a narrow, longitudinal, symmetrical ideal tripole configuration by setting the anode intensities A1, A2 to non-zero values, setting the anode intensities A3, A4 to zero values, setting the above and below anode focuses AF, BF to relatively small equal values, and defining the relative position between the central ideal cathode and the electrode array 26, such that the central ideal cathode is transversely aligned with the right inner electrode column 26'.

The fourth ideal tripole configuration S4 can be defined as a wide symmetrical ideal tripole configuration by setting the anode intensities A1, A2 to non-zero values, setting the anode intensities A3, A4 to zero values, setting the above and below anode focuses AF, BF to relatively large equal values, and defining the relative position between the central ideal cathode and the electrode array 26, such that the central ideal cathode is transversely aligned with the right outer electrode column 12.

The ideal quadpole configuration S5 can be defined to have two ideal anodes that longitudinally flank the central ideal cathode, and a third ideal anode positioned to the left of the central ideal cathode equidistantly from the two anodes by setting the anode intensities A1, A2, A3 to non-zero values, setting the anode intensity A4 to a zero value, setting the above and below anode focuses AF, BF to relatively large equal values, setting the left anode focus LF to a relatively small value, and defining the relative position between the central ideal cathode and the electrode array 26, such that the central ideal cathode is transversely aligned with the right inner electrode column 26'.

The ideal multipole configurations illustrated in FIG. 22b may be considered critical points between which the anode intensities (A1-A4), anode focuses (LF, RF, AF, BF), and the cathode advancement are incrementally changed to smoothly advance the VOA from a medial position to a lateral position, as best shown in FIG. 22c.

In particular, between the first ideal tripole configuration S1 and the second ideal tripole configuration S2, the above and below anode intensities A1, A2 are maintained at zero values (remain turned off), the left and right anode intensities A3, A4 are maintained at non-zero values (remain turned on), the left anode focus LF is incrementally increased to a relatively high value while the right anode focus RF is incrementally decreased to a relatively low value, and the position of the ideal central cathode is incrementally shifted to the right.

Between the second ideal tripole configuration S2 and the third ideal tripole configuration S3, the above and below anode intensities A1, A2 are incrementally increased from the zero values (gradually turned on) while the left and right anode intensities A3, A4 are incrementally decreased to zero values (gradually turned off), the left and right anode focuses LF, RF are maintained, and the position of the ideal central cathode is maintained.

Between the third ideal tripole configuration S3 and the fourth ideal tripole configuration S4, the non-zero values of the above and below anode intensities A1, A2 are maintained (remain turned on), the zero values of the left and right anode intensities A3, A4 are maintained (remain turned off), the left anode focus LF is incrementally decreased while the right anode focus RF is incrementally increased, the above and below anode focuses AF, BF are incrementally increased, and the position of the ideal central cathode is incrementally shifted to the right.

Between the fourth ideal tripole configuration S4 and the ideal quadpole configuration S5, the above and below anode intensities A1, A2 are incrementally decreased to lesser non-zero values (gradually turned down, e.g., by 5-50%), the left anode intensity A3 is incrementally increased from the non-zero value (gradually turned up, e.g., by 10-100%), the zero value of the right anode intensity A4 is maintained (remained turned off), all the anode focuses AF, BF, LF, RF are maintained, and the position of the ideal central cathode is maintained.

When electrical energy is conveyed to the electrode array 26 in accordance with stimulation parameter sets computed to emulate the sequence of ideal tripole configurations and quadpole configuration, a volume of activation (VOA) will be incrementally displaced medio-laterally across the spinal cord of the patient in concordance with the incremental displacement of the ideal cathode.

It should be appreciated that it is important that, during the current steering methodologies described with respect to FIGS. 14-22, none of the poles of the ideal multipole configurations is outside of the maximum extent of the electrode array 26.

For example, if the surgical paddle lead 12 illustrated in FIG. 3 is conventionally implanted within the patient such that the electrode columns are aligned with the longitudinal axis of the spinal cord, it is important that an ideal pole not extend above electrodes E1 and E17 (which may occur when current is steered in the rostral direction), not extend below electrodes E6 and E22 (which may occur when current is steered in the caudal direction), not extent to the left of the left electrode column 26" (which may occur when current is steered in the lateral direction to the left), and not extend to the right of the right electrode column 26" (which may occur when current is steered in the lateral direction to the right). If the percutaneous leads 12 illustrated in FIG. 4 are implanted with the patient such that the leads are aligned with the longitudinal axis of the spinal cord and the distal ends of the leads are pointed in the rostral direction (as shown in FIG. 2), it is important that an ideal pole not extend above electrodes E1 and E9 (which may occur when current is steered in the rostral direction), and not extend below electrodes E8 and E16 (which may occur when current is steered in the caudal direction). It can be appreciated from this that, in the case of a linear electrode array (e.g., any of the electrode columns of the surgical paddle lead or percutaneous leads), the maximum extent will be coincident with an electrode 26 at the end of the linear electrode array (e.g., for the surgical paddle lead 12, electrodes E1 and E6 for the left outer electrode column 26", electrodes E7 and E11 for the left inner electrode column 26', electrodes E12 and E16 for the right inner electrode column 26', and electrodes E17 and E22 for the right outer electrode column 26"; and electrodes E1 and E8 for the percutaneous lead 12(1); and electrodes E9 and E16 for the percutaneous lead 12(2)).

Referring to FIG. 23, to prevent any ideal pole from extending outside the maximum extent of the electrode array 26, the control circuitry 50 first sequentially defines a plurality of ideal multipole configurations relative to the electrode array 26; e.g., in the manner described above with respect to FIG. 15. The control circuitry 50 then determines a spatial relationship between at least one of the defined plurality of ideal multipole configurations and the maximum extent of the electrode array 26, and if any pole of a defined ideal multipole configuration will spatially exceed the maximum extent of the electrode array 26, the control circuitry 50 modifies the plurality of ideal multipole configurations such that all of the defined ideal multipole configurations that spatially exceeded the maximum extent of the electrode array 26 will spatially be within the maximum extent of the electrode array 26. As can be seen from FIG. 23, if the defined ideal multipole configurations remain unmodified, the upper pole (anode) of the wide upper ideal bipole configuration $B_{1u}$ and the upper pole (anode) of the wide ideal bipole configuration $T_{2.5}$ extend above the rostral-most electrode (i.e., the maximum allowed rostral focus). As shown in FIG. 24, the sequence of ideal bipole/tripole configurations is defined by the dashed trajectory line sequentially connecting the critical points (representing by circles).

The control circuitry 50 corrects this by decreasing the longitudinal focus LGF of the wide upper ideal bipole configuration $B_{3u}$ (essentially eliminating the wide upper ideal bipole configuration $B_{3u}$ and replacing it with a narrower upper ideal bipole configuration $B_{2.5u}$). The control circuitry 50 also delays the initial rostral displacement of the ideal cathode, which was previously to occur at the wide upper ideal bipole configuration $B_{3u}$, until the wide ideal tripole configuration $T_{2.5}$. To provide another step for displacing the ideal cathode before the final displacement at the wide lower ideal bipole configuration $B_{3l}$, the control circuitry 50 adds a lower ideal bipole configuration $B_{2.5l}$ between the wide ideal tripole configuration $T_{2.5}$ and the wide lower ideal bipole configuration $B_{3l}$.

As best shown in FIG. 25, the sequence of ideal bipole/tripole configurations is defined by a trajectory line sequentially connecting the critical points (representing by circles). As can be seen, the sequence beginning with the narrow ideal tripole configuration ($T_2$) and ending with the narrow upper ideal bipole configuration ($B_{2u}$) incrementally increases the upper anode percentage (UAP) while maintaining the longitudinal focus (LGF). The sequence beginning with the narrow upper ideal bipole configuration ($B_{2u}$) and ending with the (adjusted) wide upper ideal bipole configuration ($B_{2.5u}$) maintains the upper anode percentage (UAP) while incrementally increasing the longitudinal focus (LGF). The sequence beginning with the wide upper ideal bipole configuration ($B_{2.5u}$) and ending with the wide ideal tripole configuration ($T_{2.5}$) incrementally decreases the upper anode percentage (UAP) while incrementally decreasing the longitudinal focus (LGF). The sequence beginning with the wide ideal tripole configuration ($T_{2.5}$) and ending with the (adjusted) wide lower ideal bipole configuration ($B_{2.5l}$) incrementally decreases the upper anode percentage (UAP) while maintaining the longitudinal focus (LGF). The sequence beginning with the wide lower ideal bipole configuration ($B_{2.5l}$) and ending with the wide lower ideal bipole configuration ($B_{3l}$) maintains the upper anode percentage (UAP) while incrementally increasing the longitudinal focus (LGF). The sequence beginning with the wide lower ideal bipole configuration ($B_{3l}$) and ending with the narrow lower ideal bipole configuration ($B_{2l}$) maintains the upper anode percentage (UAP) while incrementally decreasing the longitudinal focus (LGF).

Notably, the above-mentioned sequence maintains the same position of the ideal cathode relative to the electrode array 26 while transitioning through different types of ideal bipole/tripole configurations between the narrow ideal tripole configuration ($T_2$) and the wide ideal tripole configuration ($T_{2.5u}$) and between the wide lower ideal bipole configuration ($B_{3l}$) and the narrow lower ideal bipole configuration ($B_{2l}$), and incrementally changes the position of the ideal cathode relative to the electrode array 26 in one direction (in this case, upward) between the wide ideal tripole configuration ($T_{2.5}$) and the wide lower ideal bipole configuration ($B_{3l}$).

The sequence illustrated in FIG. 24 can be repeatedly cycled through, with the effect being that the ideal cathode is shifted upward by one electrode per each cycle. As discussed above with respect to FIG. 15, if each of ideal bipole/tripole configuration is generally aligned along the spinal cord of the patient, when electrical energy is conveyed to the electrode array 26 in accordance with stimulation parameter sets computed to emulate the sequence of bipolar/tripole configurations, a volume of activation (VOA) will be incrementally rostro-caudally displaced along the spinal cord of the patient in concordance with the incremental displacement of the ideal cathode.

As can be appreciated, by modifying the longitudinal focus (LGF), the control circuitry 50 displaces the ideal anode(s) and ideal cathode relative to each other for the respective ideal multipole configurations. In doing this, values defining a spatial relationship between the ideal anode(s) and ideal cathode (in this case, the longitudinal focus (LGF)) may be stored in memory. At least some of these values may be variable, such that the control circuitry 50 may displace the ideal anode(s) and ideal cathode relative to each other by modifying the variable values.

Figure 26:
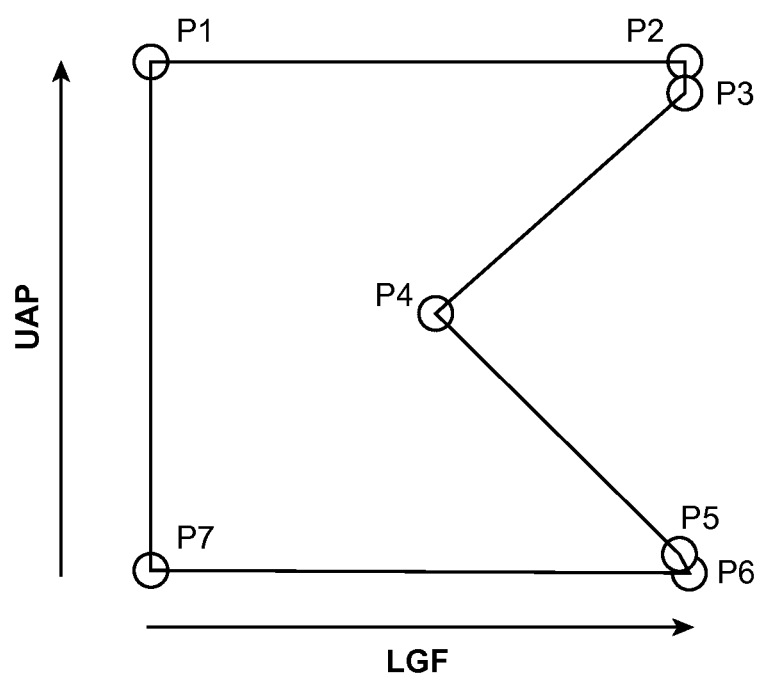
FIG. 26 is a plot illustrating a weaving space for a sequence of ideal bipole/tripole configurations that may be varied to prevent an ideal bipole/tripole configuration from exceeding the maximum extent of the electrode array.

For example, as illustrated in FIG. 26, seven critical points (P1-P7) representing seven ideal bipole/tripole configurations at any given time are shown in a weave space, defined by the longitudinal focus (LGF) and the upper anode percentage (UAP), with the sequence of ideal bipole/tripole configurations defined by a trajectory line sequentially connecting the critical points (representing by circles). Critical points P1 and P7, which represent narrow ideal bipole/tripole configurations, cannot be varied, and therefore, can be defined by fixed values stored in memory, and critical points P2-P6, which represent wide ideal bipole/tripole configurations, can be varied, and therefore, can be defined by variable values stored in memory.

In the illustrated embodiment, critical points P1, P7 initially represent a narrow lower ideal bipole configuration and a narrow upper ideal bipole configuration; critical points P2, P3 initially represent identical wide upper ideal bipole configurations, critical point P4 initially represents a wide ideal tripole configuration, and critical points P5, P6 initially represent identical wide lower ideal bipole configurations. Initially, it is assumed that the maximum longitudinal focus (LGF) in both the rostral and caudal direction is above a certain limit. The control circuitry 50 may change the variable values associated with critical points P2-P6, such that no pole of an ideal bipole/tripole configuration exceeds the maximum longitudinal focus (LGF) (i.e., the maximum extent of the electrode array 26). In the illustrated embodiment, the variable values associated with critical points.

Figures 27A, 27B, 27C:
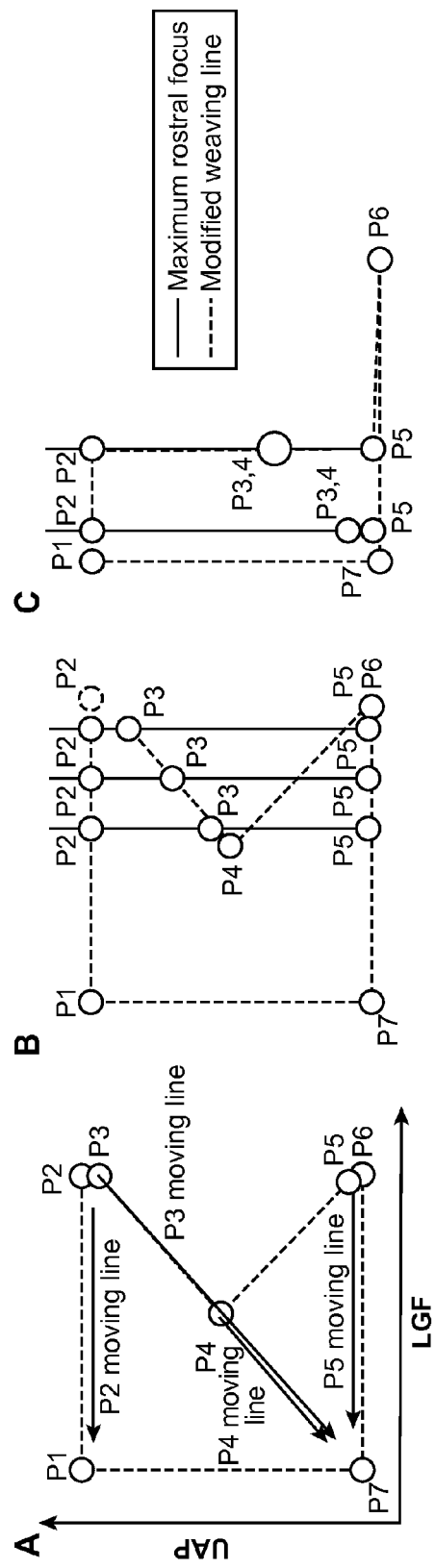
FIGS. 27a-27c are plots of a weaving space illustrating the manner in which the ideal bipole/tripole configurations are varied to prevent an ideal bipole/tripole configuration from exceeding a maximum rostral extent of the electrode array.

For example, if the maximum longitudinal focus at issue is a rostral longitudinal focus (i.e., the upper poles of the ideal bipole/tripole configurations may possibly exceed the upper maximum extent of the electrode array 26), critical points P2, P5 may be displaced horizontally left along the respective P2, P5 moving lines (thereby decreasing the respective longitudinal focus values (LGFs), and the critical point P3, P4 may be displaced diagonally left and downward along the respective P3, P4 moving lines (thereby decreasing the respective longitudinal focus values (LGFs) and decreasing the upper anode percentages (UAPs), as shown in FIG. 27a.

When the rostral maximum longitudinal focus (LGF) is less than the longitudinal focus (LGF) of critical point P2, critical points P2, P5 are concurrently displaced along the respective P2, P5 moving lines to the same longitudinal focus (LGF) value (thereby effectively narrowing the wide upper and lower ideal bipole configurations), and critical point P3 is displaced along the P3 moving line (effectively changing the upper ideal bipole configuration into a narrower ideal tripole configuration). If the rostral maximum longitudinal focus (LGF) is less than the longitudinal focus (LGF) of critical point P4, critical point P4 is displaced along the P4 moving line (effectively narrowing the wide ideal tripole configuration). In this case, the critical points P3, P4 are concurrently displaced along the respective P3, P4 moving lines to the same longitudinal focus (LGF) value and the same upper anode percentage (UAP) value. In effect, the critical points P3, P4 will represent the identical ideal tripole configuration.

As shown in FIG. 27b, critical points P2, P3, P5 are displaced in accordance with three different rostral maximum longitudinal focuses (LGFs) (represented by vertical solid lines) that are between the longitudinal focuses (LGFs) of critical points P2, P4. As shown in FIG. 27c, critical points P2, P3, P4, P5 are displaced in accordance with two different rostral maximum longitudinal focuses (LGFs) (represented by vertical solid lines) that are less than the longitudinal focus (LGF) of critical point P4. Shifting of the ideal cathode may be applied between critical points P3, P6. A modified weaving trajectory line sequentially connects the modified critical points P1-P7 shown in FIGS. 27b and 27c.

Figures 28A, 28B, 28C:
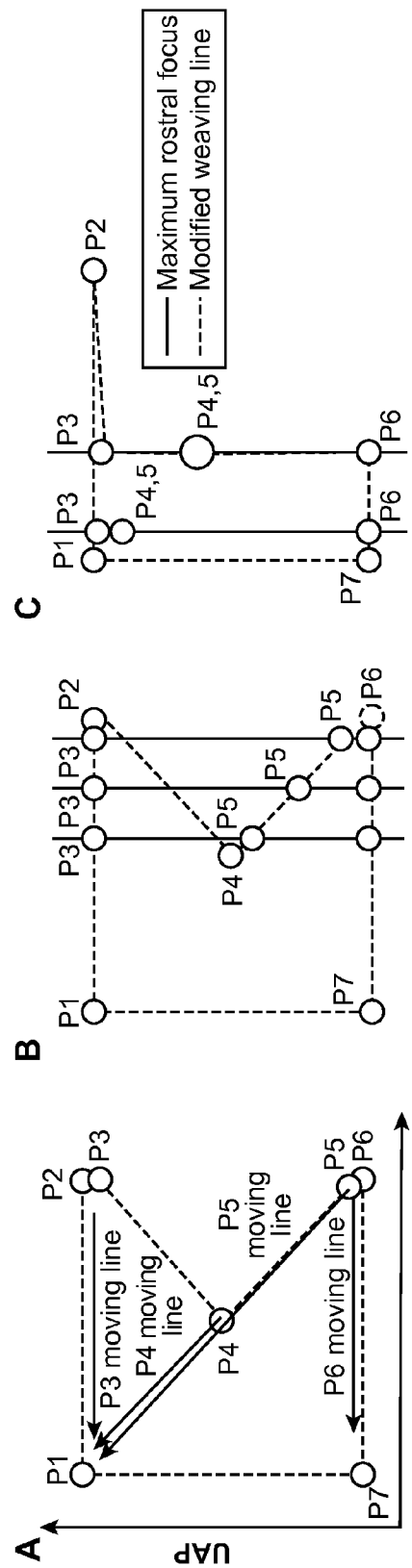
FIGS. 28a-28c are plots of a weaving space illustrating the manner in which the ideal bipole/tripole configurations are varied to prevent an ideal bipole/tripole configuration from exceeding a maximum caudal extent of the electrode array.

As another example, if the maximum longitudinal focus at issue is a caudal longitudinal focus (i.e., the lower poles of the ideal bipole/tripole configurations may possibly exceed the lower maximum extent of the electrode array 26), critical points P3, P6 may be displaced horizontally left along the respective P3, P6 moving lines (thereby decreasing the respective longitudinal focus values (LGFs) and decreasing the respective upper anode percentages (UAPs), and the critical point P4, P5 may be displaced diagonally left and upward along the respective P4, P5 moving lines (thereby decreasing the respective longitudinal focus values (LGFs) and increasing the respective upper anode percentages (UAPs), as shown in FIG. 28a.

When the caudal maximum longitudinal focus (LGF) is less than the longitudinal focus (LGF) of critical point P6, critical points P3, P6 are concurrently displaced along the respective P3, P6 moving lines to the same longitudinal focus (LGF) value (thereby effectively narrowing the wide upper and lower ideal bipole configurations), and critical point P5 is displaced along the P5 moving line (effectively changing the lower ideal bipole configuration into a narrower ideal tripole configuration). If the rostral maximum longitudinal focus (LGF) is less than the longitudinal focus (LGF) of critical point P4, critical point P4 is displaced along the P4 moving line (effectively narrowing the wide ideal tripole configuration). In this case, the critical points P4, P5 are concurrently displaced along the respective P4, P5 moving lines to the same longitudinal focus (LGF) value and the same upper anode percentage (UAP) value. In effect, the critical points P4, P5 will represent the identical ideal tripole configuration.

As shown in FIG. 28b, critical points P3, P5, P6 are displaced in accordance with three different rostral maximum longitudinal focuses (LGFs) (represented by vertical solid lines) that are between the longitudinal focuses (LGFs) of critical points P4, P6. As shown in FIG. 28c, critical points P2, P3, P4, P5 are displaced in accordance with two different rostral maximum longitudinal focuses (LGFs) (represented by vertical solid lines) that are less than the longitudinal focus (LGF) of critical point P4. Shifting of the ideal cathode may be applied between critical points P3, P6. A modified weaving trajectory line sequentially connects the modified critical points P1-P7 shown in FIGS. 28b and 28c.

Notably, there may be times when the anodes of the ideal bipole/tripole configurations must be eliminated from the sequence, because the ideal cathode is too close to the maximum extent of the electrode array 26. For example, as shown in FIG. 29, as a result of the ideal cathode being too close to the maximum rostral extent of the electrode array 26, the upper anode of the ideal bipole/tripole configurations cannot be used. In this case, the sequence of ideal bipole/tripole configurations shown in FIG. 24 will be limited to lower ideal bipole configurations (i.e., the narrow lower ideal bipole configuration ($B_{2l}$), (adjusted) wide lower ideal bipole configuration ($B_{2.5l}$), and wide lower ideal bipole configuration ($B_{3l}$).

As best shown in FIG. 30, the sequence of ideal lower bipole configurations is defined by a trajectory line sequentially connecting the critical points (representing by circles). As can be seen, the sequence beginning with the narrow lower ideal bipole configuration ($B_{2l}$) and ending with the (adjusted) wide lower ideal bipole configuration ($B_{2.5l}$) incrementally increases the longitudinal focus (LGF) while displacing the ideal cathode. The sequence beginning with the wide lower ideal bipole configuration ($B_{2.5l}$) and ending with the wide lower ideal bipole configuration ($B_{3l}$) further incrementally increases the longitudinal focus (LGF) while further displacing the ideal cathode. The sequence beginning with the wide lower ideal bipole configuration ($B_{3l}$) and ending with the narrow lower ideal bipole configuration ($B_{2l}$) incrementally decreases the longitudinal focus (LGF) while maintaining the ideal cathode.

Although the techniques for preventing ideal multipole configurations from exceeding the maximum extent of the electrode array 26 have been described above with respect to longitudinal bipole/tripole configurations, it should be appreciated that techniques for preventing the ideal multipole configurations from exceeding the maximum extent of the electrode array 26 can be applied to the transverse multipole configurations illustrated in FIG. 22b.

As previously discussed, it is preferable that the spacings between the poles of the ideal multiple configurations (i.e., the focuses) match the effective separation between the electrodes 26. In performing this function, the CP 18 is capable of estimating an effective electrode separation between the physical electrodes 26 and estimating an effective electrode separation at an arbitrary point in space bounded by the physical electrodes 26.

Figure 31A:
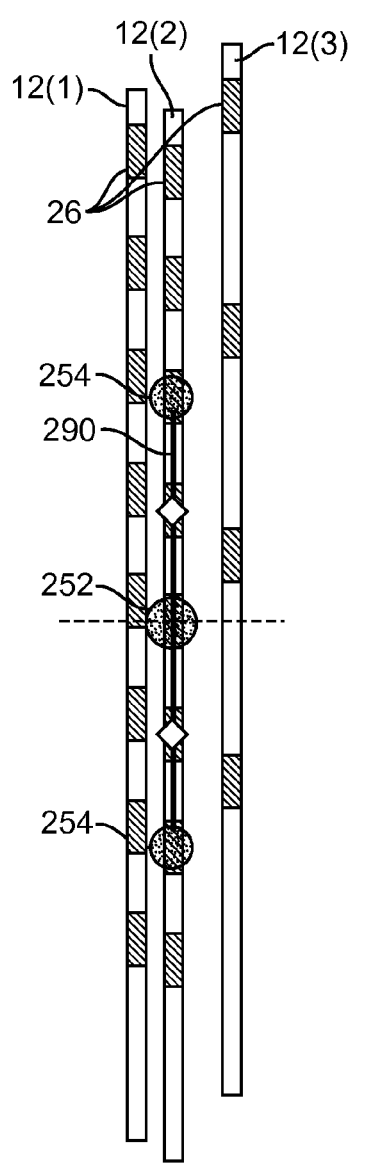
FIG. 31a is a plan view of three percutaneous neurostimulation leads and an ideal tripole configuration aligned with the center neurostimulation lead, wherein the separation between the poles of the ideal tripole configuration is the same as the electrode spacing of the center neurostimulation lead.
Figure 31B:
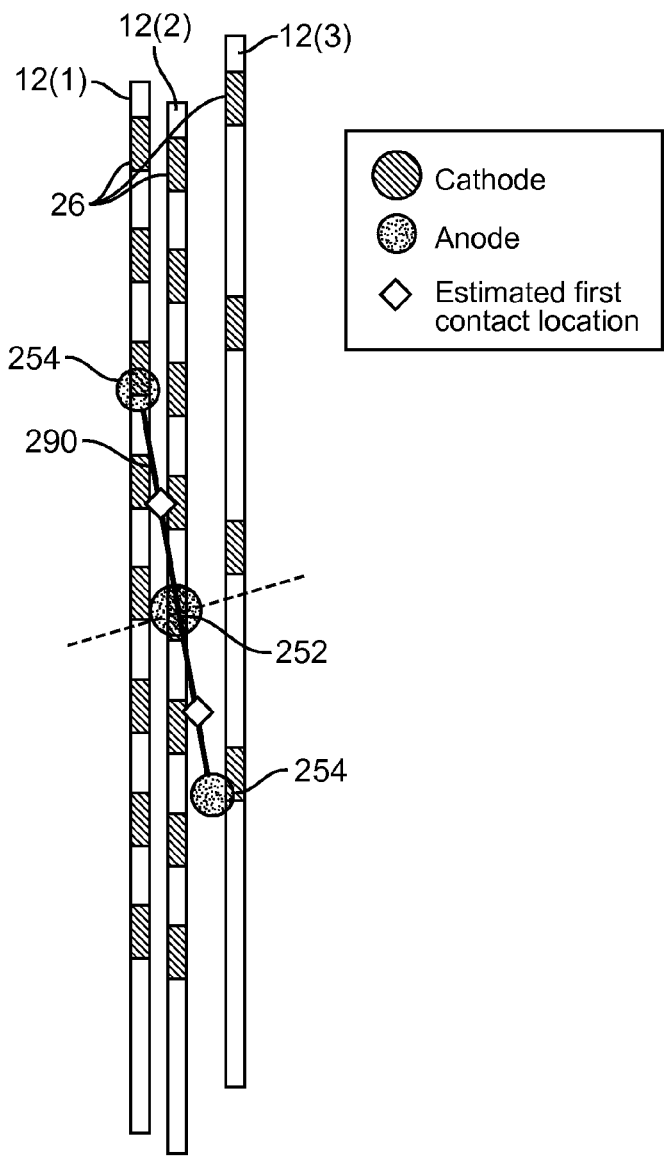
FIG. 31b is a plan view of three staggered percutaneous neurostimulation leads and an ideal tripole configuration rotated relative to the center neurostimulation lead, wherein the separation between the poles of the ideal tripole configuration is not the same as the electrode spacing of the center neurostimulation lead.

Referring first to FIGS. 31a and 31b, an ideal longitudinal tripole configuration is shown relative to three percutaneous neurostimulation leads 12(1)-12(3) that are longitudinally staggered relative to each other. As shown, neurostimulation leads 12(1) and 12(2) carry eight electrodes 26 each, and the neurostimulation lead 12(3) carries four electrodes 26.

As shown in FIG. 31a, when the pole axis 290 along which the poles of the ideal tripole configuration are aligned is parallel to the longitudinal axis of the center lead 12(2), with the ideal cathode 252 being located on one of the electrodes 26 (center electrode), assuming that a longitudinal focus equal to a two electrode separation is desired, the effective electrode separation is estimated to simply be the same as the electrode separation for the center lead 12(2), so that the ideal anodes 254 are located over the second electrodes from the center electrode over which the ideal cathode 252 is located.

However, as shown in FIG. 31b, when the pole axis 290 has been rotated relative to the longitudinal axis of the center lead 12(2), with the ideal cathode 252 being located on one of the electrodes 26, the effective electrode separation is estimated based on the available electrodes 26 along the pole axis 290. To obtain a longitudinal focus with a two electrode separation, an initial effective electrode separation from the center electrode is estimated along the pole axis 290 to obtain an estimation of the first electrode location (represented by the diamond), and then a second effective electrode separation from the estimated first electrode location is then estimated to obtain an estimation of the second electrode location.

Figure 32A:
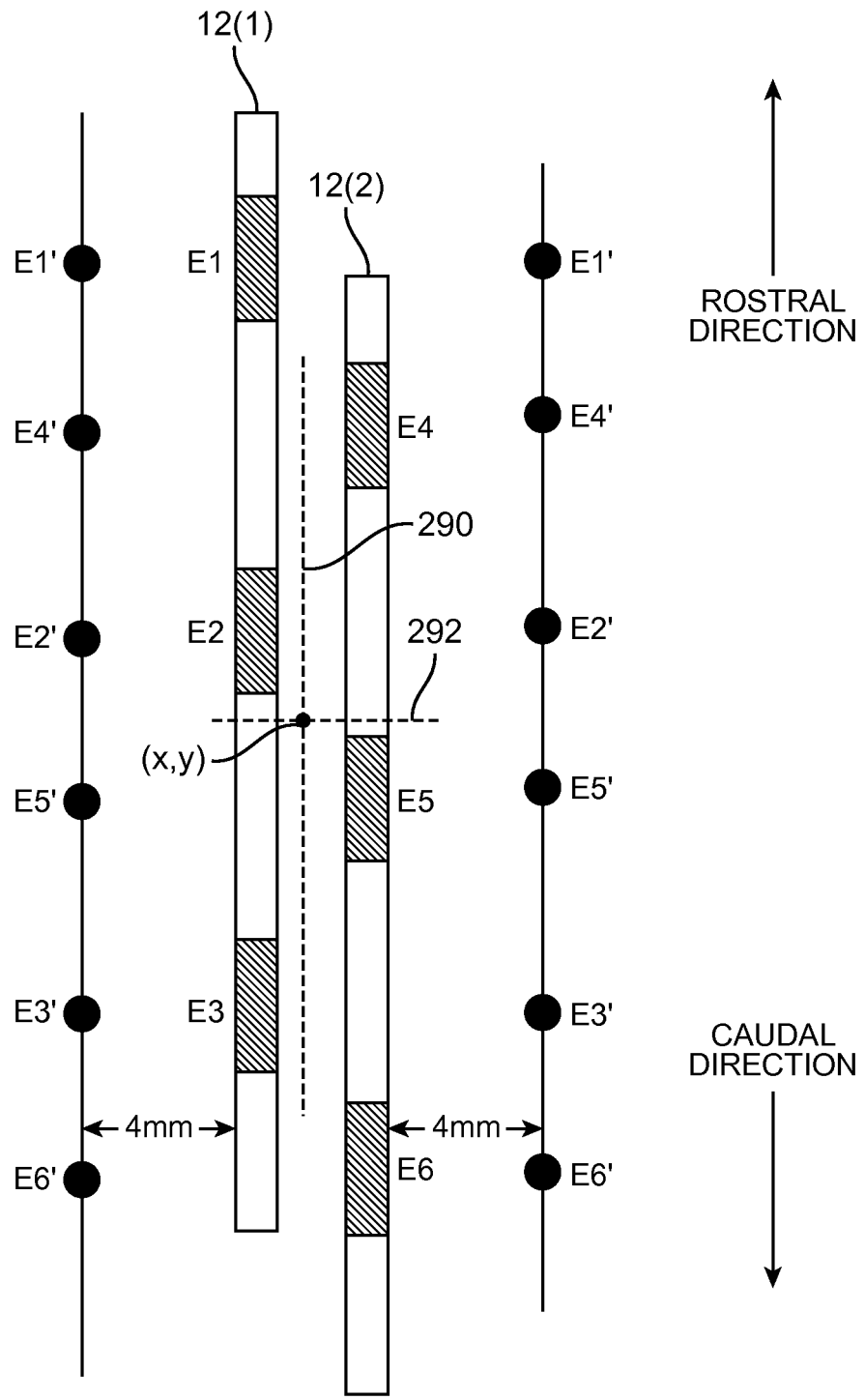
FIG. 32a is a plan view of two staggered percutaneous neurostimulation leads with a point in space at which an effective electrode separation can be estimated in the rostral direction or the caudal direction.

With reference to FIG. 32a, two staggered neurostimulation leads 12(1), 12(2) are shown with a total of six electrodes E1-E6. It is assumed that the CP 18 will define an ideal multipole configuration relative to the electrodes E1-E6 in alignment with a pole axis 290. In the illustrated embodiment, the neurostimulation leads 12(1), 12(2) are parallel to each other and/or the pole axis 290 is parallel to the neurostimulation leads 12(1), 12(2). However, it should be noted that the neurostimulation leads 12(1), 12(2) may be non-parallel to each other and/or the pole axis 290 may be non-parallel to either of the neurostimulation leads 12(1), 12(2).

In attempting to match the focus of the ideal multiple configuration with the effective electrode separation along the pole axis 290, the CP 18 designates each of the electrodes E1-E6 as a reference electrode, estimates an effective electrode separation at each of the E1-E6, estimates an effective electrode separation at a point in space (x,y) along the pole axis 290 (presumably, where one pole of the ideal multiple configuration is located) based on the estimated effective electrode separation at each of the reference electrodes E1-E6, and defines the spacing between the poles (i.e., the focus) of the ideal multiple configuration based on the estimated effective electrode separation at the point in space (x, y) along the pole axis 290.

In the illustrated embodiment, the CP 18 estimates the effective electrode separation at each of the reference electrodes E1-E6 by computing a weighted average of actual separations between each respective reference electrode and the indexed ones of the electrodes. For each reference electrode, the CP 18 will select only the electrodes that are located in the direction in which the effective electrode separation is estimated. In the illustrated embodiment, the CP 18 selects, as the indexed electrodes, only the electrodes located on one side of a line 292 intersecting the respective reference electrode and perpendicular to the pole axis 290; that is, all of the electrodes above the line 292 if the effective electrode separation in the rostral direction is estimated, and all of the electrodes below the line 292 if the effective electrode separation in the caudal direction is estimated. For example, if the current reference electrode is electrode E5, and the effective electrode separation is to be estimated in the rostral direction, the CP will determine the respective spacings between reference electrode E5 and indexed electrodes E1, E2, and E4, which are all above the line 292. If the current reference electrode is electrode E5, and the effective electrode separation is to be estimated in the caudal direction, the CP will determine the respective spacings between reference electrode E5 and indexed electrodes E3 and E6, which are both below the line 292.

Figure 32B:
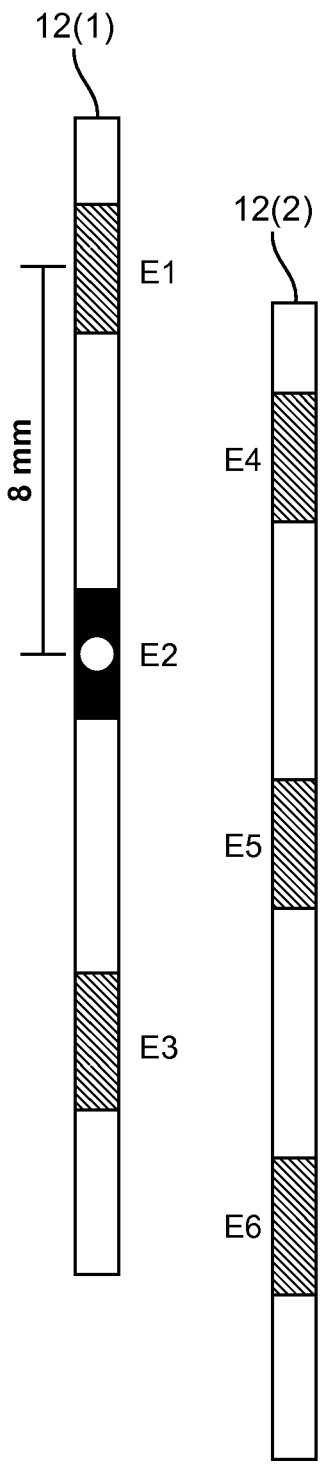
FIG. 32b is a plan view of two widely spaced staggered percutaneous neurostimulation leads, wherein electrodes on the right neurostimulation lead is not taken into account when estimating an effective electrode separation at a reference electrode on the left neurostimulation lead.
Figure 32C:
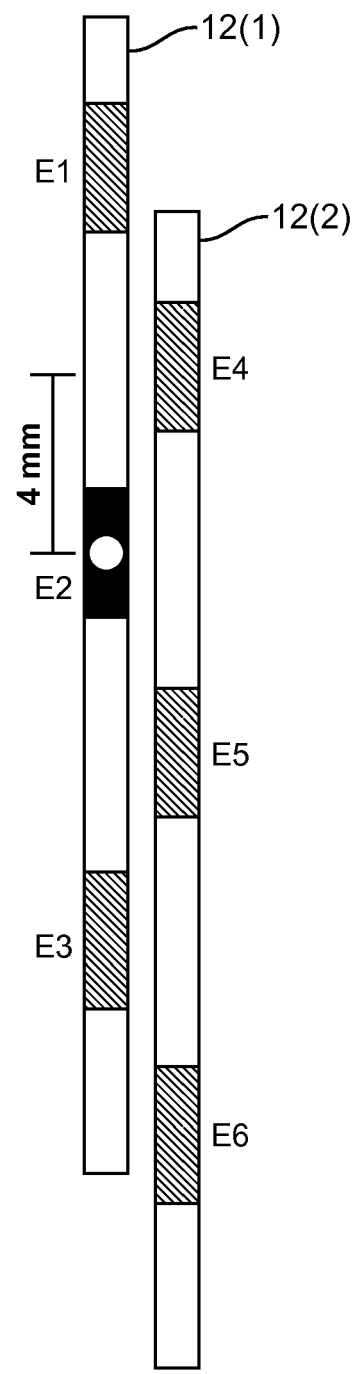
FIG. 32c is a plan view of two narrowly spaced staggered percutaneous neurostimulation leads, wherein an electrode on the right neurostimulation lead dominates the estimation of an effective electrode separation at a reference electrode on the left neurostimulation lead.

For each reference electrode, weighting values are given to the indexed electrodes in accordance with the separation between the reference electrode and the indexed electrode, such that the indexed electrodes that are relatively close to the reference electrode are given relatively high weighting values, and the indexed electrodes that are relatively far from the reference electrode are given relatively low weighting values. Thus, it can be appreciated when the neurostimulation leads 12 are widely spaced apart, as shown in FIG. 32b, the indexed electrodes on the right neurostimulation lead 12(2) may be too far from a reference electrode (in this case, electrode E2 represented by the circle) on the left neurostimulation lead 12(1) to be considered, and thus, the effective electrode separation will approach the nominal electrode separation on the neurostimulation leads 12 (e.g., 8 mm). When the neurostimulation leads 12 are narrowly spaced apart, as shown in FIG. 32c, the indexed electrodes on the right neurostimulation lead 12(2) may be close enough to the reference electrode (in this case, electrode E2 represented by the circle) on the left neurostimulation 12(1) to dominate, and thus, the effective electrode separation will approach the separation between the reference electrode E2 and electrode E4 (e.g., 4 mm if electrode E4 is equidistance between electrodes E1 and E2).

Figure 33:
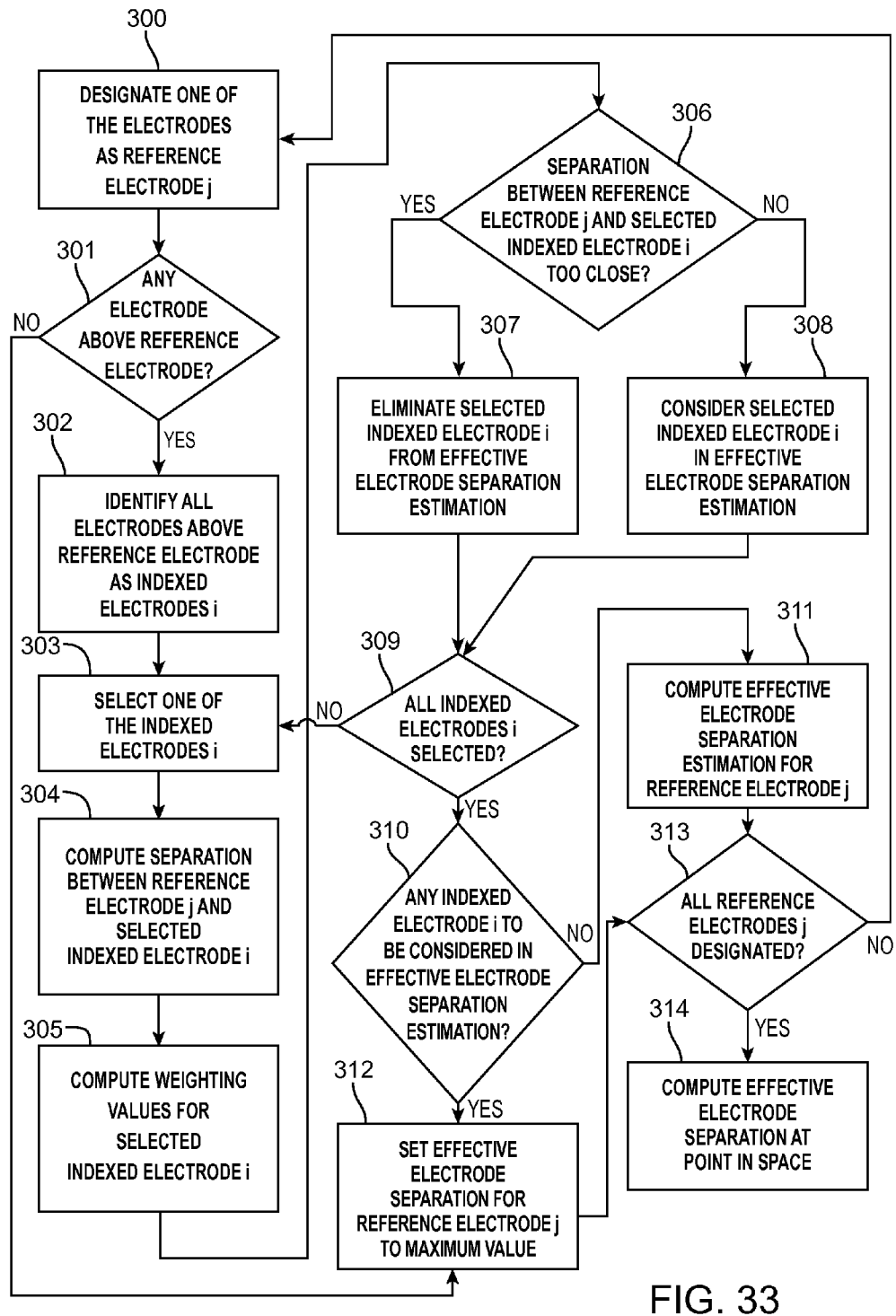
FIG. 33 is a flow diagram illustrating one method performed in the CP of FIG. 8 to estimate an effective electrode separation at a point in space, which can be utilized to define a spacing between one pole located at the point in space and another pole of an ideal multipole configuration.

Referring to FIG. 33, one method of estimating the effective electrode separation of electrodes E1-E6 at a point in space (x,y) in the rostral direction will now be described.

First, one of the electrodes E1-E6 is currently designated as a reference electrode j (step 300). Next, it is determined whether there are any electrodes above the currently designated reference electrode j, and in particular, above a line that is perpendicular to the pole axis and intersects the currently designated reference electrode j (step 301). If there are any electrodes above the currently designated reference electrode j, all of these electrodes are identified as indexed electrodes j to be compared to the currently designated reference electrode j (step 302). Next, one of the indexed electrodes i is selected (step 303), and the actual separation between the currently designated reference electrode j and the currently selected indexed electrode i is computed (step 304).

In the illustrated embodiment, the actual separation is represented by a first directional component $d_x$ perpendicular to the pole axis 290 and a second directional component $d_y$ perpendicular to the pole axis 290. The first directional component $d_x$ can be computed in accordance with the equation: $d_x=|x-E_x(i)|$, where x is the coordinate of the currently designated reference electrode j along an axis perpendicular to the pole axis 290, and $E_x$ is the coordinate of the currently selected indexed electrode i along an axis perpendicular to the pole axis 290. The second directional component $d_y$ can be computed in accordance with the equation: $d_y=|y-E_y(i)|$, where y is the coordinate of the currently designated reference electrode j along an axis parallel to the pole axis 290, and $E_y$ is the coordinate of the currently selected indexed electrode i along an axis parallel to the pole axis 290.

Then, weighting values $W_x$ and $W_y$ for the indexed electrode i are respectively computed from the first directional separation component $d_x$ and second directional separation component $d_y$ (step 305). The weighting value Wx for the indexed electrode i can be computed in accordance with the equation: $W_x(i)=e^{(-d_x \cdot \lambda_x)}$, where $\lambda_x$ is a constant. The weighting value Wy for the indexed electrode i can be computed in accordance with the equation: $W_y(i)=e^{(-d_y \cdot \lambda_y)}$, where $\lambda_y$ is a constant. In the illustrated embodiment, $\lambda_x$ is greater than $\lambda_y$. For example, $\lambda_x$ may be equal to 5, and $\lambda_y$ may be equal to 1. In this manner, the component of the actual spacing along the pole axis 202 is weighted greater than the component of the actual spacing perpendicular to the pole axis 202.

Notably, because there is a limit to how close ideal poles can be before electrical performance degrades, it is important that electrodes that are too close to the reference electrode be eliminated from the effective electrode separation estimation. To this end, it is determined whether the separation, and in particular the second directional component $d_y$, of the actual separation, between the selected indexed electrode i and the currently designated reference electrode j is less than a minimum threshold value (e.g., 3.8 mm) (step 306). If the second directional component $d_y$ is less than the minimum threshold value, the currently selected indexed electrode i is eliminated from the effective electrode separation estimation by designating a discrete weighting value $w_c(i)=0$ (step 307). If the second directional component $d_y$ is not less than the minimum threshold value, the currently selected indexed electrode i is considered in the effective electrode separation estimation by designating a discrete weighting value $w_c(i)=1$ (step 308).

Next, it is determined whether all of the indexed electrodes i have been selected for comparison with the currently designated reference electrode j (step 309). If not, steps 303-308 are repeated for the next indexed electrode i. If so, it is determined whether any of the selected indexed electrodes i has been selected to be considered in the electrode separation estimation (i.e., whether any indexed electrode i has a non-zero discrete weighting $w_c(i)$) (step 310). If at least one selected indexed electrode i has a non-zero discrete weighting $w_c(i)$, the effective electrode separation at the currently designated reference electrode j is estimated by computing a weighted average of actual separations between the currently designated reference electrode j and indexed electrodes i in accordance with the equation (step 311):

$$S_e = \frac{\sum_{i}^{N} W_x(i) \cdot W_y(i) \cdot W_c(i) \cdot d_y(i)}{\sum_{i}^{N} W_x(i) \cdot W_y(i)}.$$

If there are no electrodes above the currently designated reference electrode j, as determined in step 301, or if no indexed electrode i has a non-zero discrete weighting $w_c(i)$, as determined in step 310, the effective electrode separation at the currently designated reference electrode j is set to a maximum value (e.g., 12 mm) (step 312).

Next, it is determined whether all the electrodes have been designated as reference electrodes j (step 313). If not, steps 300-312 are repeated for the next reference electrode j. If so, an effective electrode separation at a point in space (x, y) along the pole axis 290 is determined by computing a weighted average of the estimated effective electrode separations at all of the reference electrodes j in accordance with the equation:

$$S_s = \frac{\sum_i^N W_x(j) \cdot W_y(j) \cdot S_e(j)}{\sum_i^N W_x(j) \cdot W_y(j)},$$

where $S_s$ is the effective electrode separation at the point in space, j is the index for one of the reference electrodes, N is the total number of the reference electrodes, $W_x$ is a weighting value as a function of the first directional component of the distance between the point in space and the reference electrode j, $W_y$ is a weighting value as a function of the second directional component of the distance between the point in space and the reference electrode j, and $S_e$ is the estimated effective electrode separation at the reference electrode j.

In the illustrated embodiment, the weighting values $W_x$ and $W_y$ are computed in accordance with the equations: $W_x(j)=e^{(-|x-E_x(j)|\cdot\lambda_x)}$ and $W_y(j)=e^{(-|y-E_y(j)|\cdot\lambda_y)}$, where $\lambda_x$ and $\lambda_y$ are constants, x is the coordinate of the point in space along an axis perpendicular to the pole axis 290, y is the coordinate of the point in space along the pole axis 290, $E_x$ is the coordinate of the position of the reference electrode j along an axis perpendicular to the pole axis 290, and $E_y$ is the coordinate of the position of the reference electrode j along the pole axis 290.

To prevent the effective electrode separation at a point in space from exceeding a maximum value, maximum electrode separations at a plurality of imaginary reference electrodes (E1'-E6') surrounding the actual reference electrodes j can be assumed, as illustrated in FIG. 32a. In the illustrated embodiments the total number of imaginary reference electrodes E1'-E6' are twice the total number of actual reference electrodes. In particular, a pair of imaginary reference electrodes is associated with each actual reference electrode. The pair of imaginary reference electrodes are aligned with the y-coordinate of the respective actual reference electrode, and are respectively located on two lines 294 that are parallel to the pole axis 290 and located outside of the actual reference electrodes (e.g., a left line that is 4 mm to the left of the left-most reference electrode, and a right line that is 4 mm that is 4 mm to the right of the right-most reference electrode). The maximum effective electrode separation at each respective imaginary reference electrode can be selected to be a maximum value (e.g., 12 mm). The imaginary reference electrode can be taken into account when estimating the effective electrode separation in space by including the imaginary reference electrodes in addition to the actual reference electrodes in the estimation.

Assuming that the point in space (x, y) is coincident with a pole of the ideal multipole configuration (e.g., an ideal cathode in an upper anode bipole configuration or tripole configuration) to be defined, the location of the other pole (e.g., an ideal anode) can be set to be a distance in the rostral direction equal to the estimated effective electrode separation at the point in space (x, y). In the case where it is desirable to define the location of an pole in the caudal direction, the effective electrode separation at the point in space (x, y) is performed in the same manner discussed with respect to FIG. 32, with the exception that the electrodes below each currently designated reference electrode j are selected as the indexed electrodes i, and in particular, below a line that is perpendicular to the pole axis and intersects the respective designated reference electrode j.

Although the foregoing techniques have been described as being implemented in the CP 18, it should be noted that this technique may be alternatively or additionally implemented in the RC 16, and the processing functions of the technique can even be performed in the IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for an electrical neurostimulator coupled to a plurality of electrodes implanted within tissue of a patient, comprising:
  a user-controlled input device configured for generating directional control signals; and
  control circuitry configured for sequentially defining a plurality of different ideal multipole configurations that includes two orthogonal ideal tripole configurations relative to the plurality of electrodes in response to the directional control signals, generating a plurality of stimulation parameter sets respectively corresponding to the plurality of different ideal multipole configuration, each stimulation parameter set defining relative amplitude values for the plurality of electrodes that emulate the respective multipole configuration, and instructing the electrical neurostimulator to convey electrical energy to the plurality of electrodes in accordance with the plurality of stimulation parameter sets, such that a locus of a volume of activation (VOA) will be incrementally displace along the tissue of the patient.

2. The system of claim 1, wherein the control circuitry is configured for sequentially defining the different multipole configurations in the following order: a first ideal tripole configuration oriented in a first direction, a second ideal tripole configuration oriented in the first direction, a third ideal tripole configuration oriented in a second direction orthogonal to the first direction, and a fourth ideal tripole configuration oriented in the second direction.

3. The system of claim 2, wherein the first ideal tripole configuration is a narrow symmetrical ideal tripole configuration, the second ideal tripole configuration is a narrow asymmetrical ideal tripole configuration, the third ideal tripole configuration is a narrow symmetrical ideal tripole configuration, and the fourth ideal tripole configuration is a wide symmetrical ideal tripole configuration.

4. The system of claim 2, wherein the control circuitry is configured for incrementally changing a position of a central ideal cathode relative to the plurality of electrodes between the first ideal tripole configuration and the second ideal tripole configuration.

5. The system of claim 2, wherein the control circuitry is configured for maintaining the same position of a central ideal cathode relative to the plurality of electrodes between the second ideal tripole configuration and the third ideal tripole configuration.

6. The system of claim 2, wherein the control circuitry is configured for incrementally changing a position of a central ideal cathode relative to the plurality of electrodes between the third ideal tripole configuration and the fourth ideal tripole configuration.

7. The system of claim 2, wherein the control circuitry is configured for incrementally changing a position of a central ideal cathode in one direction relative to the plurality of electrodes between the first ideal tripole configuration and the second ideal tripole configuration, and incrementally changing the position of the central ideal cathode in the one direction relative to the plurality of electrodes between the third ideal tripole configuration and the fourth ideal tripole configuration.

8. The system of claim 7, wherein the control circuitry is configured for maintaining the same position of a central ideal cathode relative to the plurality of electrodes between the second ideal tripole configuration and the third ideal tripole configuration.

9. The system of claim 2, wherein the control circuitry is configured for defining a quadpole configuration after the fourth ideal tripole configuration in response to the control signals.

10. The system of claim 9, wherein the control circuitry is configured for maintaining the same positions of a central cathode and two anodes relative to the plurality of electrodes between the fourth ideal tripole configuration and the ideal quadpole configuration.

11. The system of claim 10, wherein the quadpole configuration includes an anode positioned equidistant between the two anodes.

12. The system of claim 1, wherein the user-control input device includes a control element, a continual actuation of which generates the directional control signals.

13. The system of claim 1, wherein the user-controlled input device comprises one or more of a graphical arrow, a joystick, a touchpad, a button pad, a group of keyboard arrow keys, a mouse, a roller ball tracking device, and horizontal and vertical rocker-type arm switches for generating the directional control signals.

14. The system of claim 1, further comprising telemetry circuitry, wherein the control circuitry is configured for transmitting the plurality of stimulation parameter sets to the neurostimulation device via the telemetry circuitry.

15. The system of claim 1, further comprising a housing containing the user input device and the control circuitry.

16. A method of providing therapy to a patient using a plurality of electrodes implanted adjacent a spinal cord of the patient, comprising:
generating directional control signals;
sequentially defining a plurality of different ideal multipole configurations relative to the plurality of electrodes in response to the directional control signals, wherein the plurality of different ideal multipole configurations includes a first ideal tripole configuration medio-laterally oriented relative to the spinal cord and a second ideal tripole configuration rostro-caudally oriented relative to the spinal cord;
generating a plurality of stimulation parameter sets respectively corresponding to the plurality of ideal multipole configurations; and
instructing the electrical neurostimulator to convey electrical energy to the plurality of electrodes in accordance with the plurality of stimulation parameter sets, thereby emulating the respective ideal multipole configurations, such that a locus of a volume of activation (VOA) will be incrementally displaced relative to the spinal cord of the patient.

17. The method of claim 16, further comprising sequentially defining the different multipole configurations in the following order: a first ideal tripole configuration oriented medio-laterally relative to the spinal cord, a second ideal tripole configuration oriented medio-laterally relative to the spinal cord, a third ideal tripole configuration oriented rostro-caudally relative to the spinal cord, and a fourth ideal tripole configuration oriented rostro-caudally relative to the spinal cord.

18. The method of claim 17, wherein the first ideal tripole configuration is a narrow symmetrical ideal tripole configuration, the second ideal tripole configuration is a narrow asymmetrical ideal tripole configuration, the third ideal tripole configuration is a narrow symmetrical ideal tripole configuration, and the fourth ideal tripole configuration is a wide symmetrical ideal tripole configuration.

19. The method of claim 17, further comprising incrementally changing a position of a central ideal cathode relative to the plurality of electrodes between the first ideal tripole configuration and the second ideal tripole configuration.

20. The method of claim 17, further comprising maintaining the same position of a central ideal cathode relative to the plurality of electrodes between the second ideal tripole configuration and the third ideal tripole configuration.

21. The method of claim 17, further comprising incrementally changing a position of a central ideal cathode relative to the plurality of electrodes between the third ideal tripole configuration and the fourth ideal tripole configuration.

22. The method of claim 17, further comprising:
incrementally changing a position of a central ideal cathode in a medio-lateral direction between the first ideal tripole configuration and the second ideal tripole configuration; and
incrementally changing the position of the central ideal cathode in rostro-caudal direction between the third ideal tripole configuration and the fourth ideal tripole configuration.

23. The method of claim 22, further comprising maintaining the same position of a central ideal cathode relative to the plurality of electrodes between the second ideal tripole configuration and the third ideal tripole configuration.

24. The method of claim 17, further comprising defining a quadpole configuration after the fourth ideal tripole configuration in response to the control signals.

25. The method of claim 24, further comprising maintaining the same positions of a central cathode and two anodes relative to the plurality of electrodes between the fourth ideal tripole configuration and the ideal quadpole configuration.

26. The method of claim 25, wherein the quadpole configuration includes an anode positioned equidistant between the two anodes.

27. The method of claim 16, further comprising continually actuating a control element to generate the directional control signals.

28. The method of claim 16, wherein the conveyance of the electrical energy to the plurality of electrodes in accordance with the plurality of stimulation parameter sets incrementally medio-laterally displaces a volume of activation (VOA) across the spinal cord.

* * * * *